United States Patent [19]

Broersma, Jr. et al.

[11] Patent Number: 5,681,925
[45] Date of Patent: Oct. 28, 1997

[54] TRIFUNCTIONAL ANTITHROMBIN AND ANTIPLATELET PEPTIDES

[75] Inventors: Robert J. Broersma, Jr.; Thomas J. Owen, both of Cincinnati, Ohio; John L. Krstenansky, Palo Alto, Calif.

[73] Assignee: Merrell Pharmaceuticals Inc., Cincinnati, Ohio

[21] Appl. No.: 502,989

[22] Filed: Jul. 17, 1995

Related U.S. Application Data

[63] Continuation of Ser. No. 76,066, Jun. 11, 1993, abandoned.
[51] Int. Cl.$^6$ .......................... A61K 38/36; A61K 38/16; C07K 14/00
[52] U.S. Cl. .......................... 530/324; 530/326; 514/12; 514/13
[58] Field of Search .......................... 530/324, 326; 514/12, 13

[56] References Cited

U.S. PATENT DOCUMENTS

| | | |
|---|---|---|
| 4,668,662 | 5/1987 | Tripier . |
| 4,767,742 | 8/1988 | Dodt et al. . |
| 4,792,525 | 12/1988 | Ruoslahti et al. . |

FOREIGN PATENT DOCUMENTS

| | | |
|---|---|---|
| 0276014 | 7/1988 | European Pat. Off. . |
| 0332523 | 9/1989 | European Pat. Off. . |
| 0333356 | 9/1989 | European Pat. Off. . |
| 0341607 | 11/1989 | European Pat. Off. . |
| 0347376 | 12/1989 | European Pat. Off. . |
| 0372503 | 6/1990 | European Pat. Off. . |
| 0372670 | 6/1990 | European Pat. Off. . |
| 0382451 | 8/1990 | European Pat. Off. . |
| 0421366 | 4/1991 | European Pat. Off. . |
| 0421367 | 4/1991 | European Pat. Off. . |
| 468327 | 1/1992 | European Pat. Off. . |
| 468448 | 1/1992 | European Pat. Off. . |
| 9008772 | 8/1990 | WIPO . |
| 9015072 | 12/1990 | WIPO . |
| 9102750 | 3/1991 | WIPO . |
| 9119734 | 12/1991 | WIPO . |
| 9201712 | 2/1992 | WIPO . |
| 9207874 | 5/1992 | WIPO . |
| 9210575 | 6/1992 | WIPO . |

OTHER PUBLICATIONS

Maraganore, et al. *Biochemistry* 29, 1990, 7095–7101.
Furie, et al, *Journal Biol. Chem* 257, 3875–82; 1982.
DiMaio, et al. *Journal Biol Chem* 265, 21698–21703.
Plow, et al., *PNAS*, vol. 82, 8057–61. 1985.
Sharma et al., "Usefulness and tolerability of Hirulog, a Direct Thrombin–Inhibitor, in Unstable Angina Pectoris" *Am. J. Cardiol.* 72, 1357–1360 (1993).
Cannon et al., "Anticoagulant Effects of Hirulog,* a Novel Thrombin Inhibitor, in Patients with Coronary Artery Disease" *Am. J. Cardiol.* 71, 778–782 (1993).
Shuman et al., "Highly Selective Tripeptide Thrombin Inhibitors", *J. Med. Chem.* 36, 314–319 (1993).

Church et al., "Chimeric Antithrombin Peptide", *J. Biol. Chem.* 266, 11975–11979 (1991).
Andrieux et al., "Amino Acid Sequences in Fibrinogen Mediating Its Interaction with Its Platelet Receptor, GPI-IbIIIa", *J. Biol. Chem.* 264, 9258–9265 (1989).
Timmons et al., "Antiplatelet 'Hybrid' Peptides Analogous to Receptor Recognition Domains on γ and α Chains of Human Fibrinogen", *Biochemistry* 28, 2919–2923 (1989).
Knapp et al., "Hirudisins", *J. Biol. Chem.* 267, 24230–24234 (1992).
Szewczuk et al., "Design of a Linker for Trivalent Thrombin Inhibitors: Interaction of the Main Chain of the Linker with Thrombin", *Biochemistry* 32, 3396–3404 (1993).
Bode et al., "The refined 1.9 Å crystal structure of human α–thrombin: interaction with D–Phe–Pro–Arg chloromethylketone and significance of the Tyr–Pro–Pro–Trp insertion segment", *The EMBO Journal* 8, 3467–3475 (1989).
Krstenansky et al., "Anticoagulant Peptides: Nature of the Interaction of the C–Terminal Region of Hirudin with a Noncatalytic Binding Site on Thrombin", *J. Med. Chem.* 30, 1688–1691 (1987).
Owen et al., "N–Terminal Requirements of Small Peptide Anticoagulants Based on Hirudin$_{54-65}$", *J. Med. Chem.* 31, 1009–1011 (1988).
Mao et al., "Interaction of Hirudin with Thrombin: Identification of a Minimal Binding Domain of Hirudin That Inhibits Clotting Activity", *Biochemistry* 27, 8170–8173 (1988).
Krstenansky et al., "Development of MDL 28,050, a Small Stable Antithrombin Agent Based on a Functional Domain of the Leech Protein, Hirudin", *Thrombosis and Haemostasis* 63, 208–214 (1990).
Maraganore et al., "Anticoagulant Activity of Synthetic Hirudin Peptides", *J. Biol. Chem.* 264, 8692–8698 (1989).
Jakubowski et al., "Inhibition of Coagulation and Thrombin–Induced Platelet Activities by a Synthetic Dodecapeptide Modeled on the Carboxy–Terminus of Hirudin", *Blood* 75, 399–406 (1990).
Altenburger et al., "General Synthesis of Polyfunctionalized Fluoromethyleneketone Retroamides as Potential Inhibitors of Thrombin", *Tetrahedron Letters* 32, 7255–7258 (1991).
Kettner et al., "The Selective Inhibition of Thrombin by Peptides of Boroarginine", *J. Biol. Chem.* 265, 18289–18297 (1990).
Barker et al., "Cyclic RGD Peptide Analogues as Antiplatelet Antithrombotics", *J. Med. Chem.* 35, 2040–2048 (1992).
Peishoff et al., "Investigation of Conformational Specificity at GPIIb/IIIa: Evaluation of Conformationally Constrained RGD Peptides", *J. Med. Chem.* 35, 3962–3969 (1992).

(List continued on next page.)

*Primary Examiner*—Cecilia J. Tsang
*Assistant Examiner*—Michael L. Borin
*Attorney, Agent, or Firm*—William R. Boudreaux

[57] ABSTRACT

Novel compounds which contain a thrombin catalytic-site inhibitor coupled with an anion binding exosite associating moiety via an RGD-X bridging sequence are trifunctional anticoagulants useful in treating venous or arterial thrombotic conditions.

6 Claims, 11 Drawing Sheets

OTHER PUBLICATIONS

Nicholson et al., "In Vitro and In Vivo Effects of a Peptide Mimetic (SC-47643) of RGD as an Antiplatelet and Antithrombotic Agent", *Throm. Res.* 62, 567-578 (1991).

Yamada, "Adhesive Recognition Sequences", *J. of Biol. Chem.* 266, 12809-12812 (1991).

Dennis et al., "Platelet glycoprotein IIb-IIIa protein antagonists from snake venoms: Evidence for a family of platelet-aggregation inhibitors", *Proc. Natl. Acad. Sci.* 87, 2471-2475 (1989).

Pierschbacher et al., "Influence of Stereochemistry of the Sequence Arg-Gly-Asp-Xaa on Binding Specificity in Cell Adhesion", *J. Biol. Chem.* 262, 17294-17298 (1987).

Plow et al., "Arginyl-Glycyl-Aspartic Acid Sequences and Fibrinogen Binding to Platelets", *Blood* 70, 110-115 (1987).

Ruoslahti et al., "New Perspectives in Cell Adhesion: RGD and Integrins", *Science* 238, 491-497 (1987).

Yue et al., "Characterization of the interactions of a bifunctional inhibitors with $\alpha$-thrombin by molecular modeling and peptide synthesis", *Prot. Eng.* 5, 77-85 (1992).

DiMaio et al., "Synthesis of a Homologous Series of Ketomethylene Arginyl Pseudodipeptides and Appliation to Low Molecular Weight Hirudin-like Thrombin Inhibitors", *J. Med. Chem.* 35, 3331-3341 (1992).

Kelly et al., "Antithrombotic effects of synthetic peptides targeting various functional domains of thrombin", *Proc. Natl. Acad. Sci.* 89, 6040-6044 (1992).

Kline et al., "Hirulog Peptides with Scissile Bond Replacements Resistant to Thrombin Cleavage", *Bioch. and Biophys. Res. Comm.* 177, 1049-1055 (1991).

DiMaio et al., "A new class of potent thrombin inhibitors that incorporates a scissile pseudopeptide bond", *FEBS* 282, 47-52 (1991).

Rydel et al., "Refined Structure of the Hirudin-Thrombin Complex", *J. Mol. Biol.* 221, 583-601 (1991).

Rydel et al., "The Structure of a Complex of Recombinant Hirudin and Human $\alpha$-Thrombin", *Science* 249, 277-280 (1990).

Marguerie et al., "Human Platelets Possess an Inducible and Saturable Receptor Specific for Fibrinogen", *J. Biol. Chem.* 254, 5357-5363 (1979).

Imura et al., "Synergistic Antithrombotic Properties of G4120, a RGD-Containing Synthetic Peptide, and Argatroban, a Synthetic Thrombin Inhibitor, in a Hamster Femoral Vein Platelet-Rich Thrombosis Model", *Thrombosis and Haemostasis* 68, 336-340 (1992).

Plow et al., "Cellular Adhesion: GPIIb-IIIa as a Prototypic Adhesion Receptor", *Prog. Heamost. Thromb.* 9, 117-154 (1989).

D. Collen, et al., *Thrombolysis in Cardiovascular Disease*, D. Julian, et al. (eds.), Marcel Dekker, Inc., New York (1989); pp. 45-67.

Hawiger et al., "Platelet Receptor Recognition Domains on the $\alpha$ Chain of Human Fibrinogen: Structure-Function Analysis", *Biochemistry* 28, 2909-2914 (1989).

Barker, et al., "Cyclic RGD Peptide Analogues as Antiplatelet Antithrombotics", *J. Med. Chem.*, 35, pp. 2040-2048, (1992).

Cadroy et al., "RGDV Peptide Selectivity Inhibits Platelet-dependent Thrombus Formation In Vivo", *J. Clin. Invest.* 84, 939-944 (1989).

TRIFUNCTIONAL ANTITHROMBIN AND ANTIPLATELET PEPTIDES

This is a continuation of application Ser. No. 08/076,066, filed Jun. 11, 1993, now abandoned.

FIELD OF THE INVENTION

This invention relates to novel peptides which are useful anticoagulant and antiplatelet agents.

BACKGROUND OF THE INVENTION

Anticoagulants are useful therapeutic agents in the pharmacological treatment of, for example, acute deep venous thrombosis, pulmonary embolism, acute arterial embolization of the extremities, myocardial infarction, stroke and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Platelet-mediated arterial thrombosis is a major pathogenic mechanism for the conditions listed in the aforementioned paragraph. Consequently, combining inhibition of platelet aggregation and thrombin suggests a useful approach to the design of antithrombotic agents. The binding of fibrinogen via the Arg-Gly-Asp (RGD) sequence to activated platelet glycoprotein (GP) IIb/IIIa receptors, a member of the integrin family, is an essential step of platelet aggregation induced by various agonists. F. A. Marguerie, et al., J. Biol. Chem. 254, 5357–5363 (1979); D. Collen, et al., Thrombolys in Cardiovascular Disease, D. Julian, et al. (eds.), Marcel Dekker, Inc., New York (1989); pp 45–67. This binding is inhibited by linear and cyclic RGD-containing synthetic peptides. E. F. Plow, et al., Prog. Hemostas. Thromb. 9, 117–156 (1989); E. F. Plow, et al., Proc. Natl. Acad. Sci., USA 82, 8057–8061 (1985).

Recent studies have shown that the strategy of combining thrombin inhibition and platelet glycoprotein (GP) IIb/IIIa (integrin) receptor blockade in a single hybrid peptide leads to both anticoagulant and antiplatelet activity. F. C. Church, et al., J. Biol. Chem. 266, 11975–11979 (1991). Additionally, peptide thrombin inhibitors combining the components of catalytic and anion-binding exosite sequence inhibitors have recently been reported. J. M. Maraganore, et al., Biochemistry, 29, 7095–7101 (1990) and J. DiMaio, et al., J. Biol. Chem., 265, 21698–21703 (1990). A key feature to determining the activities of these peptides was the separation of the two components that bind to the thrombin active site and exosite by a spacer of suitable length. These studies have shown that peptides containing a minimum of four amino acid residues between the catalytic site inhibitor and the anion-binding exosite sequence were necessary for maximal thrombin inhibition. These reports support the results from cross-linking studies which indicate that the distance between the $NH_2$ terminus of hirudin analogs bound to the anion-binding exosite on thrombin and the hydroxyl group of Ser-195 in the catalytic pocket of thrombin is about 18–20 Å. B. Furie, et al., J. Biol. Chem., 257, 3875–3882 (1982) and W. Bode, et al., EMBO J., 8, 3467–3475 (1989).

Patent Cooperation Treaty Application Publication Number WO 92/10575, published Jun. 25, 1992 specifically discloses trifunctional inhibitors of both platelet activation and thrombin. These inhibitors consist of a glycoprotein IIb/IIIa inhibitory moiety and a thrombin inhibitory moiety consisting of a catalytic site-directed moiety that binds to and inhibits the active site of thrombin. The catalytic site-directed moiety is bound to an anion binding exosite associating moiety via a linker moiety which has a backbone chain having a calculated length of between about 18Å and 42Å.

Applicants have discovered that when the thrombin catalytic-site inhibitor (e.g.,(D)Phe-Pro-Arg, or an analog thereof) is coupled with an anion binding exosite associating moiety (hirudin$_{55-65}$ analog) via a cyclic Arg-Gly-Asp-X "bridging" sequence, a trifunctional peptide combining both catalytic and anion-binding exosite inhibition of thrombin with platelet glycoprotein (GP) IIb/IIIa receptor inhibition is obtained. Moreover, a significant increase in the peptide's inhibition of platelet aggregation and anticoagulant activity is noted when the cysteine residues providing the disulfide linkages which join the thrombin catalytic-site inhibitor to the hirudin$_{55-65}$ analog are in the (D) configuration. An additional increase is noted when norleucine is substituted for phenylalanine in the cyclic Arg-Gly-Asp-X "bridging" sequence. This new class of compounds should provide for a useful adjunct therapy due to the dual mode of action and increased potency.

SUMMARY OF THE INVENTION

Compounds of the formula $$X—A—B—C—Y \qquad (1)$$

wherein X is an amino terminal residue selected from hydrogen, one or two alkyl groups of from 1 to 6 carbon atoms, one or two acyl groups of from 2 to 10 carbon atoms, carbobenzyloxy, $H_2NC(=NH)—$, or a t-butyloxy carbonyl group;

A is a peptide analog of the formula

$$A_1—A_2—A_3 \qquad (2)$$

wherein
$A_1$ is (D)Phe, (D)Phg, (D)1-Tiq, (D)3-Tiq, N-Me-(D)Phe, (D)Cha, (D)Chg, (D)Nag, or (D)Thg;
$A_2$ is Pro, Pip, or Azt;
$A_3$ is Arg, Lys, Orn, or hArg;
B is a peptide analog of the formulae

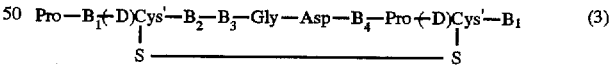

$$\text{Pro}—B_1\text{—(D)Cys'}—B_2\text{—}B_3\text{—Gly}—\text{Asp}—B_4\text{—Pro}—\text{(D)Cys'}—B_1 \qquad (3)$$
$$\phantom{\text{Pro}—B_1\text{—(D)Cys}}|\phantom{\text{—}B_2\text{—}B_3\text{—Gly}—\text{Asp}—B_4\text{—Pro}—\text{(D)Cys}}|$$
$$\phantom{\text{Pro}—B_1\text{—(D)Cy}}S\text{————————————————}S$$

or

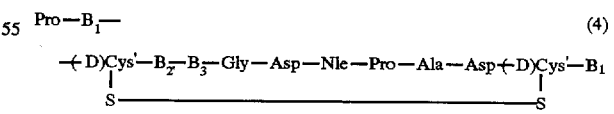

$$\text{Pro}—B_1— \qquad (4)$$
$$—\text{(D)Cys'}—B_2\text{—}B_3\text{—Gly}—\text{Asp}—\text{Nle}—\text{Pro}—\text{Ala}—\text{Asp}—\text{(D)Cys'}—B_1$$
$$\phantom{—\text{(D)Cys}}|\phantom{—B_2\text{—}B_3\text{—Gly}—\text{Asp}—\text{Nle}—\text{Pro}—\text{Ala}—\text{Asp}}|$$
$$\phantom{—\text{(D)Cy}}S\text{——————————————————}S$$

wherein
$B_1$ is Gly, Ala, (D)Ala, Val, (D)Val, or Gly-Gly;
$B_2$ is Gly, Gly-Gly, Gly-Gly-Gly, Gly-Gly-Gly-Gly or any (D) amino acid;
$B_2'$ is Arg-Ile-Pro or Lys-Ile-Pro;
$B_3$ is Arg, hArg, N-Me-Arg or Lys;
$B_4$ is Nle, Phe, Met or Cha;
C is a peptide analog of the formula $$\text{Asp}—C_1—C_2—C_3—C_4—C_5—C_6—C_7—C_8—C_9 \qquad (5)$$

wherein
$C_1$ is Phe, pClPhe, pNO$_2$Phe, Tha, Npa, Tyr or Trp;
$C_2$ is Glu or Asp;
$C_3$ is any amino acid;
$C_4$ is Ile, Val, Leu or Phe;
$C_5$ is Pro, Hyp, Sar, NMePhg or D-Ala;
$C_6$ is any amino acid;
$C_7$ is any amino acid;
$C_8$ is Tyr, Glu, Pro, Ala-Cha, Tyr-Cha, Tyr-Leu and Ala-Tyr;
$C_9$ is a bond or is Glu, (D)Glu, Gln, Pro, Leu-Gln, Asp-Glu, or Leu-Pro; and
Y is a carboxy terminal residue selected from OH, $C_1$–$C_6$ alkoxy, amino, mono- or di-($C_1$–$C_4$) alkyl substituted amino, or benzylamino;
or a pharmaceutically acceptable salt thereof are useful anticoagulant agents. This invention also relates to the use of the above compounds in treating acute postangioplasty occlusion, extracorporeal circulation-induced cytopenia, developing myocardial infarction, and post fibrinolytic therapy occlusion.

DETAILED DESCRIPTION OF THE INVENTION

Figure 1:
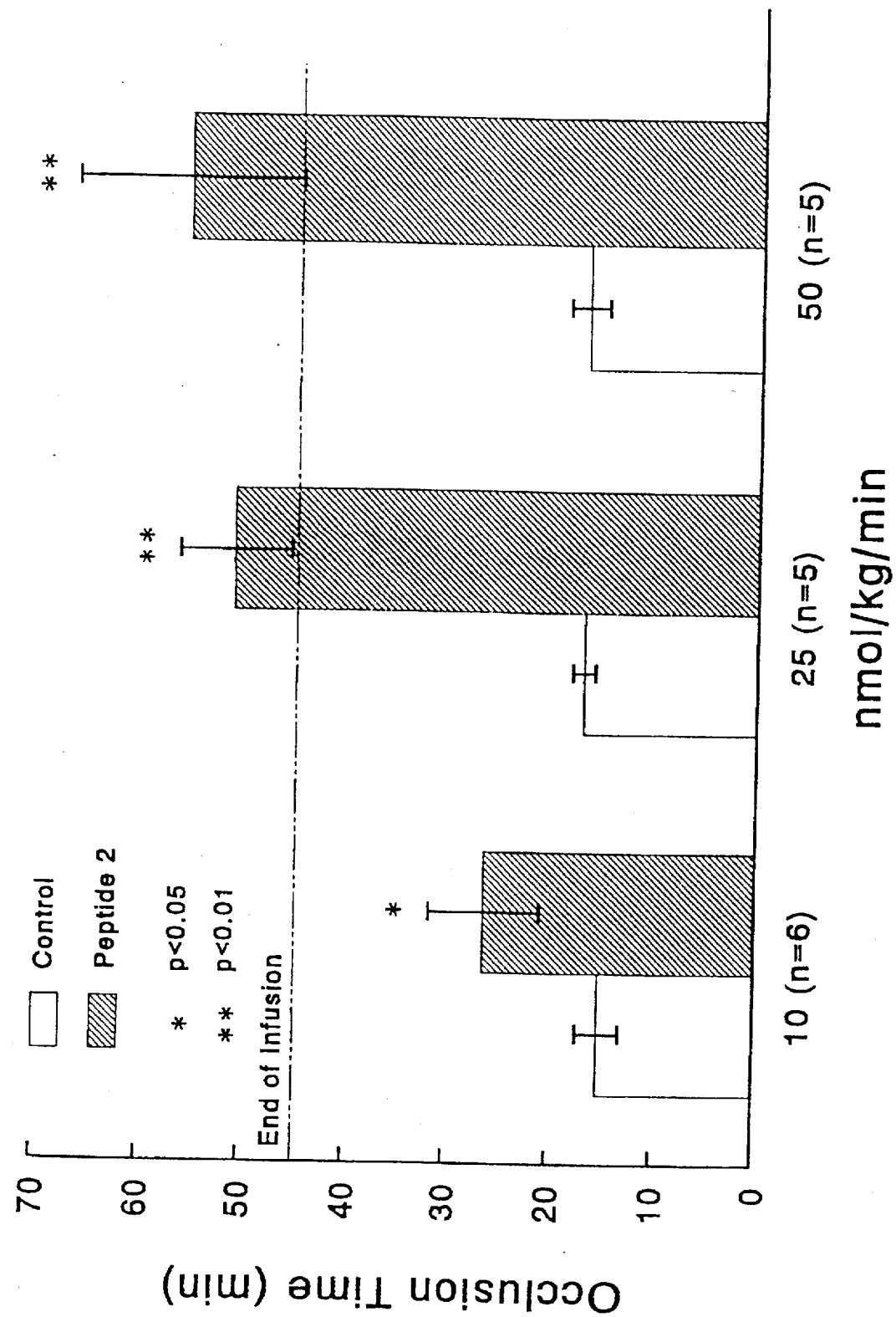
FIG. 1 shows, in bar graph form, the effect of Peptide 2 on FeCl$_3$ arterial occlusion time in rats. The control is represented by the unshaded bars while Peptide 2 is represented by the shaded bars. In this figure, p represents probability, while n represents the number of animals tested.

The following common abbreviations of the amino acids and amino and carboxy terminal groups are used throughout this specification:

Gly (or G)—glycine
Ala (or A)—alanine
Val (or V)—valine
Leu (or L)—leucine
Ile (or I)—isoleucine
Pro (or P)—proline
Phe (or F)—phenylalanine
Trp (or W)—tryptophan
Ser (or S)—serine
Met (or M)—methionine
Thr (or T)—threonine
Cys (or C)—cysteine
Tyr (or Y)—tyrosine
Gln (or Q)—glutamine
Asn (or N)—asparagine
Asp (or D)—aspartic acid
Glu (or E)—glutamic acid
Lys (or K)—lysine
Arg (or R)—arginine
His (or H)—histidine
Nle—norleucine
Chg—cyclohexylglycine
Cha—β-cyclohexyl-alanine
Pip—pipecolic acid, pipecolinic acid, or 2-piperidine carboxylic acid
Azt—2-azetidine carboxylic acid
Orn—ornithine
hArg—homoarginine
N-Me-Arg—N-methylarginine
N-Me-(D)Phe—N-methyl-D-phenylalanine
Thg—3-thienylglycine
Nag—naphthylglycine
1-Tiq—1,2,3,4-Tetrahydroisoquinoline-1-carboxylic acid
3-Tiq—1,2,3,4-Tetrahydroisoquinoline-3-carboxylic acid
Phg—phenylglycine
pClPhe—para-chloro-phenylalanine
pNO$_2$Phe—para-nitro-phenylalanine
Tha—3-(2-thienyl-alanine)
Npa—β-(2-naphthyl)alanine
Hyp—hydroxyproline
Sar—sarcosine (N-methylglycine)
N-Me-Phg—N-methyl-phenylglycine Pen—penicillamine

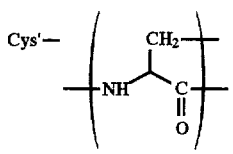

When two or more amino acids combine to form a peptide, the elements of water are removed, and what remains of each amino acid is called a residue in this application. "Residue" is therefore an amino acid that lacks a hydrogen atom of the terminal amino group, and/or lacks the hydroxyl group of the terminal carboxyl group. Using accepted terminology, a dash (-) in front of (indicating loss of a hydrogen) and/or after (indicating loss of the hydroxyl) a three letter code for an amino acid or amino acid derivative indicates a residue.

The Cys' residues are represented by formula (5) which illustrates a cysteine residue without a sulfide moiety in its R-group side chain. As is illustrated in formulae (3) and (4), the (D)Cys' residues are linked via a disulfide bond. The disulfide moiety is bonded to the (D)Cys' residues via the methylene moiety of the (D)Cys' residues, as is illustrated by formula (6):

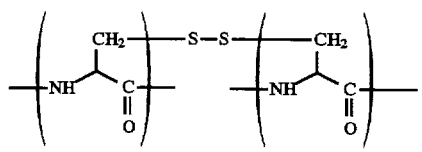

Note that formulae (5) and (6) may generically illustrate either D- or L- residues.

The following common abbreviations of various protecting groups are used throughout this specification:
Boc=t-butyloxycarbonyl
Bzl=benzyl
Mbz=p-methyl-benzyl
Chx=cyclohexyl
Tos or Tosyl=p-toluenesulfonyl
Cbz=carbobenzyloxy
BrZ=bromobenzyloxycarbonyl
Suc=succinyl
Ac=acetyl
PAM=phenylacetamidomethyl An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, acetyl, benzoyl succinyl, maleyl, and glutaryl. A halogen group is a fluoro, chloro, bromo or iodo group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or paraposition of the phenyl moiety with one or two of the following, a ($C_1$–$C_4$) alkyl, ($C_1$–$C_4$) alkoxy, halogen, or nitro groups or substituted with a methylenedioxy group, β-2- and 3-thienylalanine, β-2- and 3-furanylalanine, β-2-, 3-, and 4-pyridylalanine, β-(benzothienyl-2- and 3-yl)alanine, β-(1- and 2-naphthyl)alanine, O-alkylated derivatives of serine, threonine, or tyrosine, S-alkylated cysteine, the O-sulfate ester of tyrosine, 3,5-diiodotyrosine and the D-isomers of the naturally occurring amino acids.

The natural amino acids, with the exception of glycine, contain a chiral carbon atom. Unless otherwise specifically indicated, the optically active amino acids, referred to herein, are of the L-configuration. The stereochemistry at the carbon atom bearing the R substituent is either the D- or L-configuration. For the purpose of this disclosure, an amino acid in the D- configuration will be delineated as D-amino acid, (D)amino acid, or as a lower case letter when employing the single letter naming system, e.g. for D-phenylalanine, D-Phe, (D)Phe, or f are all acceptable deliniations. As is customary, the structure of peptides written out herein is such that the amino terminal end is on the left side of the chain and the carboxy terminal end is on the right side of the chain.

The polypeptides of formula 1 can form pharmaceutically acceptable acid addition salts with any non-toxic, organic or inorganic acid. Illustrative inorganic acids which form suitable acid addition salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower) alkylpiperidine, and any other suitable amine.

The compounds of formula 1 are novel peptides combining thrombin inhibition with an antagonism of platelet glycoprotein (GP) IIb/IIIa receptors in a single hybrid peptide. The peptides of this invention each contain a catalytic site inhibitor of thrombin (i.e. portion A) attached to an anion-binding exosite inhibitor of thrombin (i.e. portion C) via a linker moiety containing a connecting "bridge" and a cyclic RGD-X sequence as the platelet GP IIb/IIIa receptor antagonist (i.e. portion B).

Portion A describes a catalytic site-directed inhibitor of thrombin. This catalytic site-directed moiety binds to the active site of thrombin and inhibits or retards the proteolytic activity of thrombin. Portion C describes a thrombin inhibitory agent which is characterized as an anion binding exosite associating moiety. Since the permutations of portion C are structurally similar to the carboxy terminal portion of hirudin, it is surmised that portion C readily binds to the anion binding exosite on thrombin.

Portion B contains two functional portions—the connecting "bridge" between the catalytic site inhibitor (portion A) and the anion-binding exosite inhibitor (portion C) and a cyclic RGD-X glycoprotein IIb/IIIa inhibitory moiety. The connecting "bridge" between the catalytic site inhibitor (portion A) and the anion-binding exosite inhibitor (portion C) is the base of the cyclic RGD-X sequence. This bridge containing residues of the $B_1$ moiety, Pro, (D)Cys' and disulfide bonds which connect the two (D)Cys' residues of portion B, is believed to act as an appropriate spacer between the catalytic site inhibitor sequence and the anion-binding exosite recognition sequence. This connecting "bridge" contains a proline residue between the $B_1$ and the $A_3$ moieties since the naturally occurring imide bond between $A_3$ and Pro is cleaved at a much slower rate than the amide bond of other amino acid residues. It is theorized, although this invention is not bound by such theory, that the presence of this imide bond accounts for the inhibitory effect of the catalytic site-directed moiety. Of course, it is contemplated that other amide bond-replaced amino acids would operate as functional equivalents, such as reduced amides, esters, ketones and sulfides.

The cyclic RGD-X glycoprotein IIb/IIIa inhibitory moiety of portion B, i.e. those amino acid residues between the two D-Cys residues of portion B, inhibits the interaction between fibrinogen and its receptor, glycoprotein IIb/IIIa. The cyclic RGD-X glycoprotein IIb/IIIa inhibitory moiety of portion B may contain from 6 to 11 of the amino acids as specified in formulae (3) and (4). Preferably, the cyclic RGD-X glycoprotein IIb/IIIa inhibitory moiety of portion B is formula (3) and contains from 6 to 9 of the amino acids as specified in formula (3).

For the purposes of this invention, it is to be understood that $A_1$ is bonded to the amino terminal moiety (X), while $A_3$ is bonded to the Pro residue which is at the N-terminal or left side of moiety B. The Asp residue at the N-terminal or left side of moiety C is bonded to the $B_1$ residue at the C-terminal or right side of moiety B.

As with any generic group of chemical compounds, certain groups are preferred. Applicants prefer those peptide derivatives of formula (1) wherein X is a hydrogen, acetyl, succinyl, or a t-butyloxy carbonyl group;
$A_1$ is (D)Phe, (D)Chg, (D)Cha, (D)Phg, (D)1-Tiq, (D)3-Tiq, or N-Me-(D)Phe;
$A_2$ is Pro;
$A_3$ is Arg or Lys;
B is formula (3) or formula (4);
$B_1$ is Gly, Ala or Gly-Gly;
$B_2$ is Gly, Gly-Gly, or any (D) amino acid, when B is formula (3);
$B_2'$ is Arg-Ile-Pro or Lys-Ile-Pro when B is formula (4);
$B_3$ is Arg or N-Me-Arg;
$B_4$ is Nle, Phe, Cha, Met;
$C_1$ is Phe, Npa or Tyr;
$C_2$ is Glu or Asp;
$C_3$ is any amino acid;
$C_4$ is Ile or Val;
$C_5$ is Pro, Hyp, or (D)Ala;
$C_6$ is any amino acid;
$C_7$ is Glu, Asp, or Ala;
$C_8$ is Tyr, Glu, Tyr-Leu, Tyr-Cha or Ala-Cha;
$C_9$ is a bond, (D)Glu, Glu, Gln, Leu-Gln or Leu-Pro; and
Y is OK, $C_1$–$C_6$ alkoxy, or mono- or di-($C_1$–$C_4$) alkyl substituted amino.

Also preferred are those compounds of formula (1) wherein
X is a hydrogen, acetyl or a t-butyloxy carbonyl group;
$A_1$ is (D)Phe, (D)Phg, (D)3-Tiq or N-Me-(D)Phe;
$A_2$ is Pro;
$A_3$ is Arg;
B is formula (3) or formula (4);
$B_1$ is Gly;
$B_2$ is Gly, (D)Tyr, (D)Val, (D)Thr, or (D)Pro when B is formula (3);
$B_2'$ is Arg-Ile-Pro when B is formula (4);
$B_3$ is Arg or N-Me-Arg;
$B_4$ is Nle or Phe with the proviso that when $B_2$ is (D)Tyr, (D)Val, (D)Thr or (D)Pro, then $B_4$ is Nle;
$C_1$ is Phe or Tyr;
$C_2$ is Glu;
$C_3$ Ks Glu or Pro;
$C_4$ Ks Ile;
$C_5$ is Pro or (D)Ala;
$C_6$ is Glu or Ala;
$C_7$ is Glu;
$C_8$ Ks Tyr, Tyr-Leu, Tyr-Cha or Ala-Cha;
$C_9$ Ks a bond or (D)Glu; and
Y is OH, $C_1$–$C_6$ alkoxy, or mono- or di-($C_1$–$C_4$) alkyl substituted amino.

Especially preferred are those peptide derivatives of formula (1) wherein
X is a hydrogen, acetyl or a t-butyloxy carbonyl group;
$A_1$ is (D)Phe, (D)Phg, (D)3-Tiq or N-Me-(D)Phe;
$A_2$ is Pro;
$A_3$ is Arg;
B is formula (3);
$B_1$ is Gly;
$B_2$ is Gly, (D)Tyr, (D)Val, (D)Thr, or (D)Pro;
$B_3$ is Arg;
$B_4$ is Nle or Phe with the proviso that when $B_2$ is (D)Tyr, (D)Val, (D)Thr, or (D)Pro, then $B_4$ is Nle;
$C_1$ is Phe;
$C_2$ is Glu;
$C_3$ is Pro;
$C_4$ is Ile;
$C_5$ is Pro;
$C_6$ is Glu or Ala;
$C_7$ is Glu;
$C_8$ is Tyr, Tyr-Cha or Ala-Cha;
$C_9$ is a bond or (D)Glu; and
Y is OH or $C_1$–$C_6$ alkoxy.

Other especially preferred compounds are those wherein $B_4$ is Nle.

The peptides of this invention can be prepared by a variety of procedures readily known to those skilled in the art. Such procedures include, but are not limited to, the solid phase sequential procedure which can be performed using established automated methods such as by use of an automated peptide synthesizer. In this procedure an α-amino protected amino acid is bound to a resin support. The resin support employed can be any suitable resin conventionally employed in the art for the solid phase preparation of a polypeptide, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky et al., Chem. Ind. (London) 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem. Acta.* 56, 1476 (1973). For example, to prepare the polypeptide wherein the carboxy terminal end is a (D)Glu residue, a Boc-D-Glu(Bzl) is coupled to chloromethylated polystyrene as its cesium salt at approximately 50° C.

Following the coupling of the α-amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C and room temperature. Other standard cleaving reagents and conditions for removal of specific α-amino protecting groups may be used. After removal of the α-amino protecting group the other α-amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyl-oxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a two-fold to about a four-fold excess. The coupling is carried out in a medium of dimethylformamide: methylene chloride (1:1) or in dimethylformamide alone or methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin under conditions well known in the art. For example this can be accomplished by treatment of the resin bound polypeptide with a solution of 5% anisole in anhydrous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed during cleavage of the protecting group of the α-amino moiety. For example, the carboxylic hydroxyl group of Aspartic acid and Glutamic acid can be protected with a benzyl or cyclohexyl group. The preferred protecting group is benzyl.

These groups can be removed by procedures well known in the art. Typically protecting group removal is done after the peptide chain synthesis is complete. For example the peptide is deprotected concomitantly with removal of the peptide from the resin by treatment with a solution of 5% anisole in anhydrous hydrofluoric acid. The protecting groups can also be removed at any other appropriate time.

The anticoagulant and antiplatelet dose of a peptide analog of this invention is from 0.2 mg/kg to 250 mg/kg of patient body weight per day depending on the patient, the severity of the thrombobotic condition to be treated and the peptide analog selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease as well as for the treatment of, for example, coronary occulsion, by dissolving existing clots. Antiplatelet therapy is indicated for the prevention of reoccurance of myocardial infarction and stroke. Those experienced in this field are readily aware of the circumstances requiring anticoagulant and antiplatelet therapy. It is believed that the peptides of this invention would be of particular benefit in the prevention of coronary thrombosis following angioplasty, in preventing thrombocytopenia during extracorporeal circulation, post fibrinolytic therapy occlusion, and to stop or delay an evolving myocardial infarction.

The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

EXAMPLES

Examples 1–12 represent typical syntheses of the peptides of formula 1. These examples are illustrative only and are not intended to limit the invention in any way. The reagents and starting materials for examples 1–12 are readily available to one of ordinary skill in the art. As used in examples 1–12, the following terms have the meanings indicated: "DCM" refers to dichloromethane, "DIEA" refers to diisopropylethylamine, "MeOH" refers to methanol, "DCC" refers to N,N'-dicyclohexylcarbodiimide, "DMF" refers to N,N'-dimethylformamide, "HOBt" refers to 1-hydroxybenzotriazole, "TFA" refers to trifluoroacetic acid, "eq." refers to equivalents, "meq" refers to milliequivalents, "g" refers to grams, "mg" refers to milligrams, "mmol" refers to millimoles, "mL" refers to milliliters, "°C." refers to degrees Celsius, "TLC" refers to thin layer chromatography, "$R_f$" refers to retention factor, "μL" refers to microliters, "μg" refers to micrograms, "μM" refers to micromolar, "mmHg" refers to millimeters of mercury and "δ" refers to parts per million down field from tetramethylsilane.

Example 1

Preparation of:

(SEQ ID NO: 1)

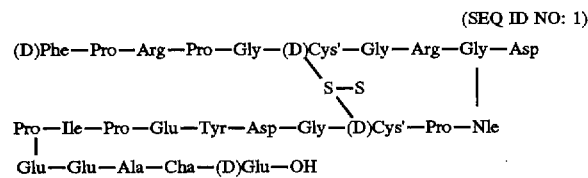

A Boc-(D)Glu(Bzl)-Pam-resin (Peninsula Laboratories, Belmont, Calif.) is elongated by stepwise deprotection and coupling of the subsequent Boc-amino acid using a Dupont 250 semi-automated peptide synthesizer according to the following protocol:

| Reagent/Solvent | Time (seconds) | # repetitions |
| --- | --- | --- |
| DCM | 30 | 1 |
| MeOH | 30 | 2 |
| DCM | 30 | 3 |

-continued

| Reagent/Solvent | Time (seconds) | # repetitions |
| --- | --- | --- |
| TFA:anisole:DCM (48:2:50) | 60 | 1 |
| TFA:anisole:DCM (48:2:50) | 1200 | 1 |
| DCM | 30 | 3 |
| DIEA:DCM (10:90) | 60 | 3 |
| DCM | 30 | 2 |
| Boc-amino acid | 1800 | 1 |
| DMF | 30 | 1 |
| DCM | 30 | 1 |
| DIEA:DCM (10:90) | 30 | 1 |
| DCM | 30 | 2 |

All Boc-amino acids are coupled as their preformed symmetrical anhydrides in two-fold excess, with the exception of Arg which is coupled in a four-fold excess as its HOBt ester. The symmetrical anhydrides are prepared as follows;

Dissolve the Boc-amino acids (4 eq) in DCM followed by addition of 0.5M DCC/DCM (2 eq). Stir the reaction for 5 minutes. Formation of the symmetrical anhydride results in precipitation of dicyclohexylurea which is removed by filtration. Then add the filtrate to the peptide resin and dilute the coupling mixture with an equal volume of DMF.

The HOBt ester of Arg is similarly formed. Dissolve Boc-Arg(Tos) (4 eq) in DCM. Add 0.5M HOBt/DMF (4 eq) and 0.5M DCC/DCM (4 eq). Remove the dicyclohexylurea by filtration, add the filtrate to the peptide resin and dilute the coupling mixture with an equal volume of DMF.

Test the peptide resin after each coupling for the presence of any free amine using Kaiser's ninhydrin procedure as is well known in the art. Amino acids are recoupled as necessary.

Following the above procedure, elongation of Boc-D-Glu (Bzl)-Pam-resin (8.06 g, 0.31 meq/gm, 2.5 mmol, purchased from Peninsula Laboratories, Belmont, Calif.) yields the peptide-resin (D)Phe[1]-Pro-Arg(Tos)-Pro-Gly[5]-(D)Cys(Mbz)-Gly-Arg(Tos)-Gly-Asp(Chx)[10]-Nle-Pro-(D)Cys(Mbz)-Gly-Asp(Chx)[15]-Tyr(BrZ)-Glu(Bzl)-Pro-Ile-Pro[20]-Glu(Bzl)-Glu(Bzl)-Ala-Cha-(D)Glu(Bzl)-Pam-Resin (19.4 g peptide resin). The following amino acids require a second coupling with one molar equivalent of their symmetrical anhydride: Boc-Cha[24], Boc-Glu(Bzl)[21], Boc-Tyr(BrZ)[16], Boc-Asp(Chx)[15], Boc-(D)Cys(Mbz)[6], Boc-Pro[4], Boc-Pro[2] and Boc-(D)Phe[1]. The coupling of Boc-Arg(Tos)[2] is repeated twice with a two-fold excess of its HOBt ester and is subsequently capped with acetic anhydride:DIEA:DCM (10:5:85).

The above prepared peptide resin (D)Phe[1]-Pro-Arg(Tos)-Pro-Gly[5]-(D)Cys(Mbz)-Gly-Arg(Tos)-Gly-Asp(Chx)[10]-Nle-Pro-(D)Cys(Mbz)-Gly-Asp(Chx)[15]-Tyr(BrZ)-Glu(Bzl)-Pro-Ile-Pro[20]-Glu(Bzl)-Glu(Bzl)-Ala-Cha-(D)Glu(Bzl)-Pam-Resin is divided into 5 portions. Each portion is cleaved, deprotected and cyclized under the following conditions. Suspend the peptide-resin (3.88 g) in anhydrous hydrofluoric acid (20 mL) in the presence of anisole (5%). Stir the reaction at about 0° C. for about 30 minutes. Then remove the hydrofluoric acid under vacuum and extract the residue with 50% acetic acid (2×10 mL), acetic acid (2×5 mL) and water (3×10 mL). Dilute the combined extracts to 1 liter with water and adjust the pH to 8.5 with ammonium hydroxide. Add $K_3Fe(CN)_6$ (1.0M, approximately 55 mL) over 15 minutes until a yellow color persists and stir at room temperature for 30 minutes. Adjust the pH to 4.0 with acetic acid. Add anion exchange resin (AG3×4A, Bio-Rad) and stir until the yellow color is removed. Collect the resin by filtration and lyophilize the filtrate to provide the crude peptide.

Dissolve the crude peptide in 50% acetic acid and apply to a Sephadex G-10 column (2.5×70 cm). Elute with 50% acetic acid at about 10.5 mL/hour. The peptide elutes at about 70–150 mL. Dilute this eluant with water and lyophilize to provide a total of 6.17 g. The desalted material is further purified by reverse phase preparative HPLC (Dynamax $C_{18}$, 21.4×250 mm, Rainin) at about 40 mL/min with gradients of 0.1% aqueous TFA/acetonitrile using a Beckman Prep 350 system to provide pure (1.3 g).

(SEQ ID NO: 1)

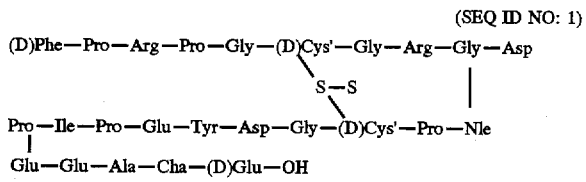

The peptide of the following examples may be prepared by the same or analogous methods.

Example 2

(SEQ ID NO: 2)

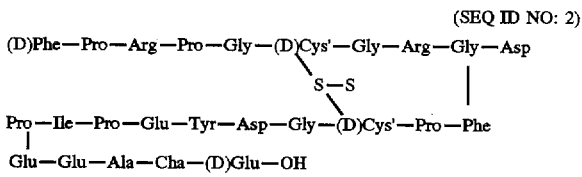

Example 3

(SEQ ID NO: 20)

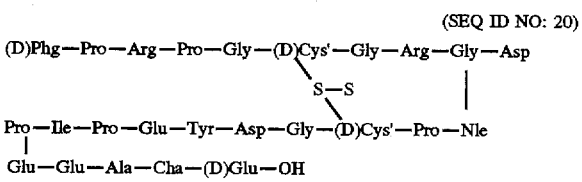

Example 4

(SEQ ID NO: 11)

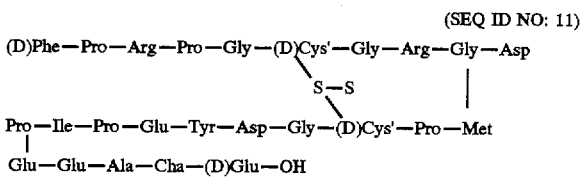

Example 5

(SEQ ID NO: 12)

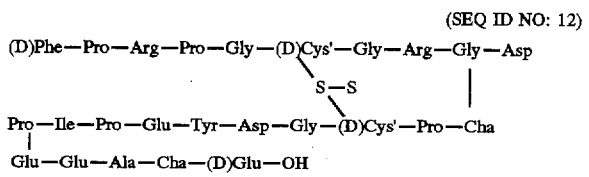

Example 6

(SEQ ID NO: 15)

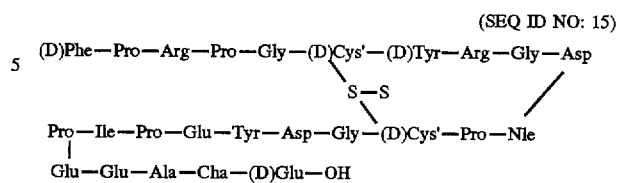

Example 7

(SEQ ID NO: 16)

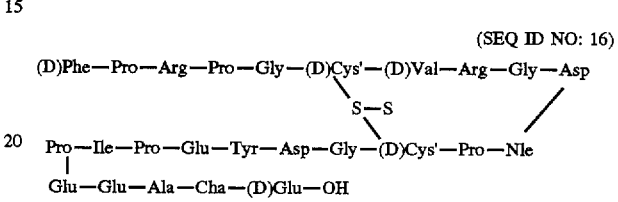

Example 8

(SEQ ID NO: 18)

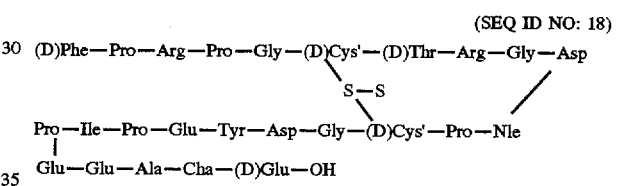

Example 9

(SEQ ID NO: 19)

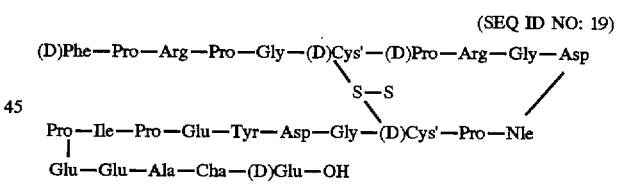

Example 10

(SEQ ID NO: 21)

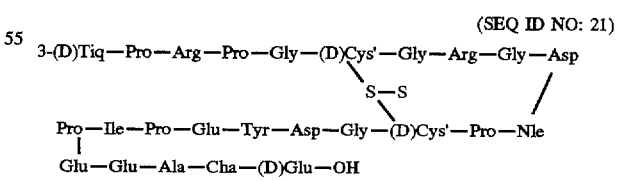

Example 11

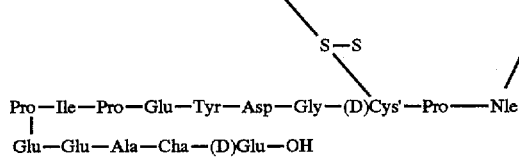

(SEQ ID NO: 22)

Example 12

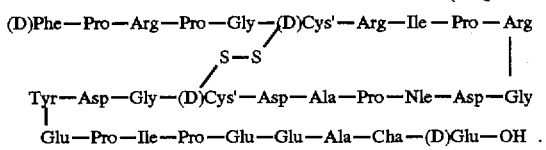

(SEQ ID NO: 10)

BIOLOGICAL

As stated above, the compounds of this invention possess the property of exhibiting significant inhibition of thrombin indicating that they are effective anti-coagulants useful for the prevention of both venous and arterial thrombotic diseases as well as unstable angina, prevention of abrupt closure of vessels after coronary angioplasty, adjunctive therapy to thrombolysis and deep vein thrombosis after orthopedic surgery. Since the compounds of this invention also contain cyclic RGD-X sequences, which are located in the linking moiety of portion B, they also act as the platelet GP IIb/IIIa receptor antagonists.

Anticoagulant and Antithrombotic Effects of the Peptide of Example 2

The peptide of example 2 (Peptide 2) (SEQ ID NO: 2), composed of a catalytic-site thrombin inhibitor (fPR) coupled to a hirudin$_{55-65}$ analog by a cyclic platelet GP IIb/IIIa receptor antagonist (RGD-X) is compared to its individual component peptides. Note that the experimental equipment noted below is merely suggested and not intended to bind or limit the invention in any way.

Experimental Animals

Male Sprague-Dawley rats (300–400 gm) may be purchased from Sprague Dawley, Inc., (Indianapolis, Ind. 46229) and used in these studies.

Blood Sampling

Blood samples may be drawn into plastic syringes containing 3.8% trisodium citrate (1:10). Plasma was prepared by centrifugation at 2,000 g-forces for 10 min. Venous blood for in vitro studies is collected from healthy, drug free, male volunteers.

Coagulation Assays

Activated partial thromboplastin time (aPTT) determinations are carried out using the reagents and methods of Dade Diagnostics, Inc. (Aguada, Puerto Rico 00602). Thrombin clotting times are determined by incubating 0.1 ml of rat plasma at 37° C. with 0.1 ml of 0.1M Tris buffer, pH 7.5 for 30 seconds. Coagulation is started with 0.1 ml of bovine thrombin (Sigma Diagnostics, St. Louis, Mo. 63178) solution (12 NIH units/ml). All clotting times are measured semiautomatically using a MLA-Electra 750 automatic coagualation timer, MLA, Inc. (Pleasantville, N.Y. 10570). The concentration required for doubling the clotting time ($ID_2$) is calculated using simple linear regression.

Platelet Aggregation

Human platelet-rich plasma (PRP) is prepared by centrifugation at 200 g-forces for 10 min. at room temperature. Platelet poor plasma (PPP) is prepared by centrifugation at 2,000 g-forces for 10 min. PRP is exposed only to plastic laboratory ware. All experiments are completed within 3 hours of blood collection. Platelet aggregation is measured photometrically using a dual channel aggregometer (Chrono-log Corp., Haverstown, Pa. 19083). One hundred percent light transmission is defined with autologus PPP. Percent maximal change in light transmission is determined from PRP following addition of ADP (1 µM) or thrombin. Thrombin (0.2–2.0 Units/ml)-induced platelet aggregation is concentration dependent and the half-maximal concentration is used for inhibition studies. Peptide 2 (SEQ ID NO: 2) is incubated with PRP (0.45 ml) for 30 seconds prior to the addition of ADP or thrombin. Aggregation is measured in a total volume of 0.5 ml. Inhibitory responses are expressed as percent inhibition when compared to a control value. The concentration resulting in 50% inhibition of aggregation. ($IC_{50}$) is calculated by simple linear regression.

$FeCl_3$ Arterial Thrombosis Model in Rats (In Vivo)

In Vivo anti-thrombotic effects of Peptide 2 (SEQ ID NO: 2) in rats is also utilized for evaluation. For example, Peptide 2 (SEQ ID NO: 2) is evaluated for antithrombotic activity in a platelet-dependent thrombin mediated $FeCl_3$-induced rat carotid artery thrombosis model according to R. J. Broersma, et al., Thromb. Res. 64, 405–412 (1991), said reference incorporated herein by reference as if fully set forth.

Results

The results from this study show that Peptide 2 (SEQ ID NO: 2) is more potent than its individual components as an anticoagulant and antithrombin in plasma coagulation and platelet aggregation assays.

With regard to the tables, the amino acid reidues within the peptide sequences are named using the single letter naming system, except for some of the modified amino acids and/or protecting groups which may be signified by the three letter naming system and enclosed by parentheses. Also, the disulfide bond connecting the (D)Cys' residues will be represented by a line drawn underneath the two (D)Cys' residues and all the residues which would be in the loop part of portion B.

TABLE I

ANTICOAGULANT ACTIVITY OF PEPTIDE 2 IN HUMAN PLASMA COMPARED WITH ITS COMPONENTS

| | | ID$_2$ μm[a] | |
|---|---|---|---|
| PEPTIDE | Peptide Sequence | aPTT | Thrombin Time |
| 2 | fPRPGcGRGDFPcGDYEPIPEEA(Cha)e | 0.060 | 0.024 |
| 2a | cGRGDFPc | — | >1,000 |
| 2b | (Suc)YEPIPEEA(Cha)e | 4 | 0.564 |
| 2c | fPRPG | >1000 | 510 |
| 2d | (CH$_3$)fPR | 2 | 0.587 |

[a]ID$_2$ value is the concentration necessary for doubling the clotting times from control in triplicate. aPTT, activated partial thromboplastin time.

With reference to Table I, the anticoagulant activity of Peptide 2 (SEQ ID NO: 2) is compared with its components —Peptide 2a (SEQ ID NO: 3), Peptide 2b (SEQ ID NO: 4), Peptide 2c (SEQ ID NO: 5), and Peptide 2d (SEQ ID NO: 6)—in assays of the activated partial thromboplastin time (aPTT) and thrombin time in normal human plasma. Peptides 2a–2d (SEQ ID NOS: 3–6) are not of this invention. Peptide 2 (SEQ ID NO: 2) doubles (ID$_2$) the aPTT and thrombin times at approximately 60 and 24 nM, respectively. Peptide 2 (SEQ ID NO: 2) is at least 20-fold more active than either 2b (SEQ ID NO: 4) or 2d (SEQ ID NO: 6) (the stable catalytic site inhibitor Me-fPR), while 2c (SEQ ID NO: 5) (the fPRPG pentapeptide) has anticoagulant activity only at much higher concetrations. Peptide 2a (SEQ ID NO: 3)(the cyclic RGD-X peptide) is inactive as an anticoagulant.

TABLE II

EFFECT OF PEPTIDE 2 ON RAT AND HUMAN COAGULATION AND PLATELET ASSAYS

| | Rat | Human |
|---|---|---|
| | ID$_2$, nM[a] | |
| Anticoagulant Activity | | |
| aPTT | 181 ± 43 | 60 ± 18 |
| Thrombin Time | 116 ± 12 | 24 ± 7 |
| | IC$_{50}$, μM[b] | |
| Inhibition of Platelet Aggregation | | |
| ADP | 65 ± 2 | 19 ± 5 |
| Thrombin | 0.014 ± .002 | 0.060 ± .026 |

[a]ID$_2$ value is the concentration necessary for doubling the clotting time from control in triplicate. aPTT, activated partial thromboplastin time.
[b]IC$_{50}$ value is the concentration necessary to inhibit platelet aggregation in PRP 50 50% of the control aggregation in duplicate.

With reference to Table II, anticoagulant studies of Peptide 2 (SEQ ID NO: 2) are performed in rat plasma. The ID$_2$ for the aPTT and thrombin time are approximately 181 and 116 nM, respectively. Thus, Peptide 2 (SEQ ID NO:. 2) is 3–5 times less active as an anticoagulant in rat plasma when compared to human plasma.

TABLE III

INHIBITION OF HUMAN PLATELET AGGREGATION

| | | IC$_{50}$ μm[a] | |
|---|---|---|---|
| Peptide | Peptide Sequence | ADP | Thrombin |
| 2 | fPRPGcGRGDFPcGDYEPIPEEA(Cha)e | 19 | 0.060 |
| 2a | cGRGDFPc | 20 | 13 |
| 2b | (Suc)YEPIPEEA(Cha)e | 895 | 3 |
| 2d | CH$_3$fPR | >1,000 | 0.2 |

IC$_{50}$ value is the concentration necessary to inhibit platelet aggregation in PRP to 50% of the control aggregation in duplicate.

As is illustrated in Table III, aggregation of human platelets induced by ADP and thrombin is inhibited by Peptide 2 (SEQ ID NO: 2). The concentration which inhibits ADP-induced platelet aggregation by 50% (IC$_{50}$) is approximately 19 μM. This is similar to the cyclic RGD-X peptide (IC$_{50}$=20 μM), Peptide 2a (SEQ ID NO: 3). The antithrombin peptides 2b (SEQ ID NO: 4) and 2d (SEQ ID NO: 6) are essentially inactive as inhibitors of ADP-induced platelet aggregation (IC$_{50}$)=895 and >1,000 μM, respectively). Peptide 2 (SEQ ID NO: 2) inhibits thrombin-induced platelet aggregation with an IC$_{50}$ value of 60 nM, and is more active than its components—Peptide 2b (SEQ ID NO: 4) (IC$_{50}$=2 μM), Peptide 2d (SEQ ID NO: 6) (IC$_{50}$=200 nM) and Peptide 2a (SEQ ID NO: 3)(IC$_{50}$=13 μM).

In contrast, aggregation of rat platelets induced by ADP and thrombin is inhibited by Peptide 2 (SEQ ID NO: 2) at IC$_{50}$=65 μM and 14 nM respectively (see Table II). Thus, Peptide 2 (SEQ ID NO: 2) is 3–4 times less active in rat plasma when compared to human platelet rich plasma.

TABLE IV

EFFECT OF PEPTIDE 2 ON ARTERIAL THROMBOSIS IN RATS

| Peptide 2 | | Occlusion Time (min) | | n animals Occluded/ |
|---|---|---|---|---|
| (nmol/kg/min)[a] | n | Control | Treated | Treated |
| 10 | 6 | 15.2 ± 2.0 | 26.3 ± 5.4* | 5/6 |
| 25 | 5 | 16.9 ± 1.1 | 50.8 ± 5.4** | 2/5 |
| 50 | 5 | 16.8 ± 1.8 | 55.5 ± 10.8*[b] | 1/5 |

Figure 2:
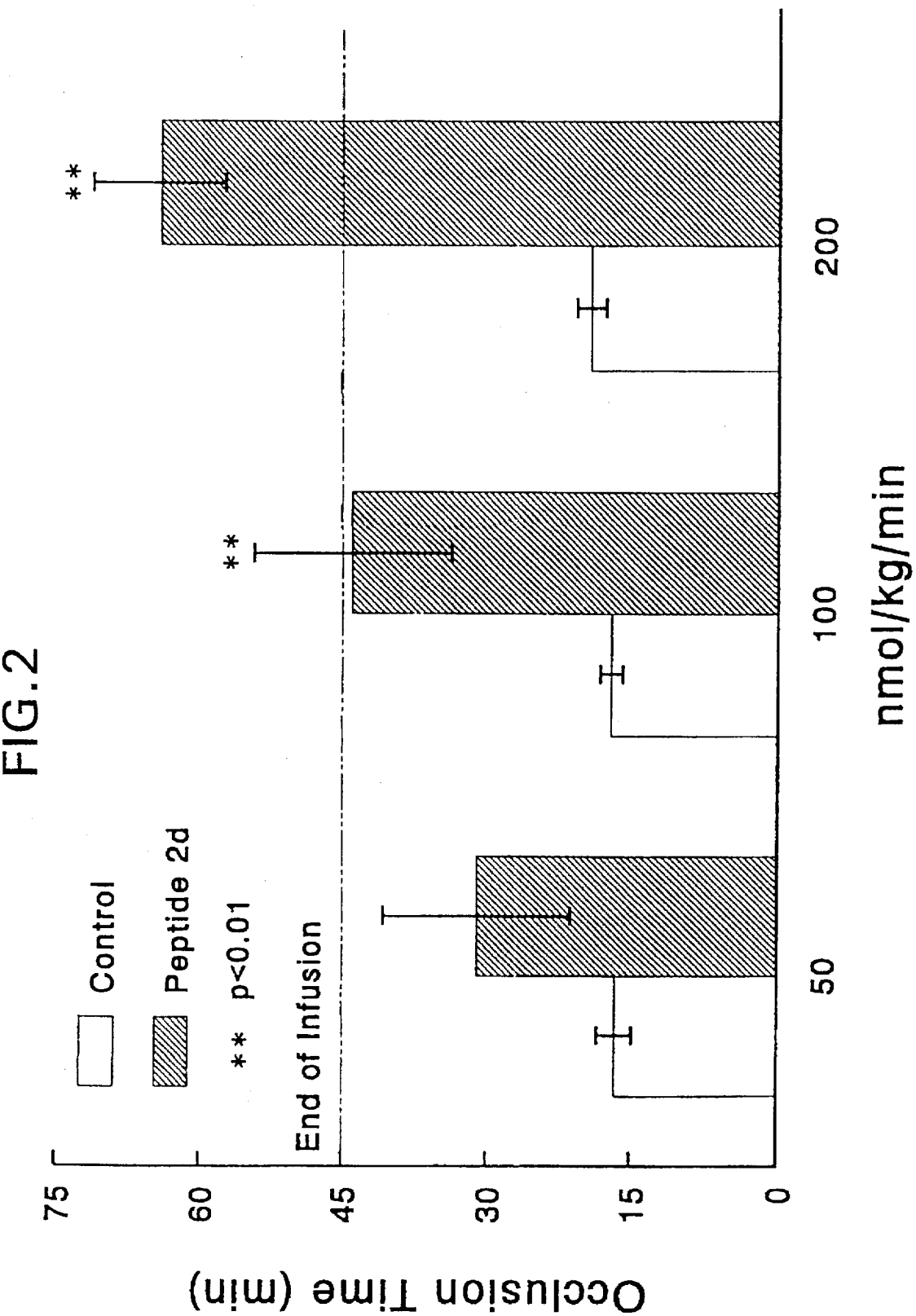
FIG. 2 shows, in bar graph form, the effect of Peptide 2d (not of this invention) on FeCl$_3$ arterial occlusion time in rats. The control is represented by the unshaded bars while Peptide 2 is represented by the shaded bars. In this figure, p represents probability, while n represents the number of animals tested.

[a]Infused over 60 min starting 15 min before FeCl$_3$ injury
[b]Occlusion time > 90 min (n = 4);
*p < 0.05 vs. control;
**p < 0.01 vs. control Peptide 2 (SEQ ID NO: 2) is evaluated for antithrombotic activity in the FeCl$_3$-induced rat carotid artery model of thrombosis. Thrombotic occlusion is dose-dependently decreased by continuous intravenous infusion of Peptide 2 (SEQ ID NO: 2) for 1 hr beginning 15 min before application of FeCl$_3$ to the artery at rakes of 10, 25, and 50 nmol/kg/min (see FIG. 1). Occlusion is prevented in four of five rats at a dose of 50 nmol/kg/min. At rates of 25 and 10 nmol/kg/min, occlusion is prevented in three of five and one of six rats, respectively. The catalytic-site antithrombin (Peptide 2d) (SEQ ID NO: 6) dose-dependently prolongs occlusion time at infusion rates of 50, 100 and 200 nmol/kg/min (see FIG. 2).

Occlusion is prevented by Peptide 2d (SEQ ID No: 6) in four of five rats at a dose rate of 50 nmol/kg/min. Neither the hirudin analog (Peptide 2b) (SEQ ID NO: 4), at 500 nmol/kg/min nor the cyclic RGD-X peptide (Peptide 2a)(SEQ ID NO: 3) at 100 nmol/kg/min prevents occlusion at these rates in this model.

TABLE V

EFFECT OF PEPTIDE 2 AND COMPONENTS ON ARTERIAL THROMBOSIS IN RATS

| Peptide | Dosage[a] | n | Occlusion Time (min) Control | Occlusion Time (min) Treated | n animals Occluded/ Treated |
|---|---|---|---|---|---|
| 2 | A | 5 | 16.8 ± 1.8 | 55.5 ± 10.8* | 1/5 |
| 2a | B | 4 | 18.5 ± 1.2 | 19.1 ± 2.0 | 4/4 |
| 2b | C | 6 | 16.9 ± 1.9 | 22.4 ± 7.1 | 5/6 |
| 2d | D | 5 | 19.3 ± 1.5 | 44.1 ± 1.0** | 1/5 |

[a]Infused over 60 min starting 15 min before $FeCl_3$ injury
*$p < 0.05$ vs. control;
**$p < 0.01$ vs. control
A - 50 nmol/kg/min, i.v.
B - 100 nmol/kg/min, i.v.
C - 500 nmol/kg/min, i.v.
D - 200 nmol/kg/min, i.v.

TABLE VI

THE EFFECT OF INTRAVENOUS PEPTIDE 2 ON COAGULATION ASSAYS[a]

| Peptide 2 nmol/kg/min | Multiple of Control aPtt[b] | Multiple of Control Thrombin Time |
|---|---|---|
| 10 | 2.9 ± 0.7(5) | 3.9 ± 0.5(5) |
| 25 | 3.6 ± 1.2(4) | 5.8 ± 1.8(4) |
| 50 | 3.7 ± 0.7(2) | 4.2 ± 0.4(2) |

[a]Blood samples taken at the end of studies on $FeCl_3$-induced arterial occlusion in rats
[b]aPTT, activated partial thromboplastin time (n = rats)

Anticoagulant and Antithrombotic Effects of the Peptide of Example 1

The peptide of example 1 (Peptide 1) (SEQ ID NO: 1), like Peptide 2 (SEQ ID NO: 2), is composed of a catalytic-site thrombin inhibitor (fPR) coupled to a hirudin$_{55-65}$ analog by a cyclic platelet GP IIb/IIIa receptor antagonist (RGD-X) is compared to its individual component peptides. However, Peptide 1 (SEQ ID NO: 1) is an analog of Peptide 2 (SEQ ID NO: 2) wherein the phenylalanine (Phe) in the cyclic RGD-X sequence of Peptide 2 (SEQ ID NO: 2) is substituted with norleucine (Nle). In this study, Peptide 1 (SEQ ID NO: 1) is compared to Peptide 2 (SEQ ID NO: 2), Peptide 3 (SEQ ID NO: 7)—an analog of Peptide 1 wherein the anion binding exosite associating moiety (portion C) is truncated—and Peptide 4 (SEQ ID NO: 8)—an analog of Peptide 1 which contains only natural L-amino acids. Additionally, Peptide 5 (SEQ ID NO: 9)—an analog of Peptide 1 (SEQ ID NO: 1) possessing a ten amino acid RGD-X loop and only natural L-amino acids) is compared to Peptide 6 (the peptide of example 12)(SEQ ID NO: 10)—an analog of Peptide 1 possessing a ten amino acid RGD-X loop) to illustrate the effects of the orientation of the RGD-X loop plays on the activity of the Peptides of this invention. Peptides 1, 2 and 6 (SEQ ID NOS: 1, 2 and 10) are of this invention while Peptides 3–5 (SEQ ID NOS: 7–9) are not of this invention. Note that the use of the experimental equipment noted below is merely suggested and not intended to bind or limit the invention in any way.

Experimental Animals

Male Sprague-Dawley rats (300–400 gm) may be purchased from Sprague Dawley, Inc., (Indianapolis, Ind. 46229) and mixed breed hounds of both sexes (6–11 kg) are used in these studies.

Dogs are anesthetized with sodium pentobarbital (30 mg/kg, i.v.). The femoral artery and both femoral veins are isolated and cannulated for the recording of blood pressure (Gould P23ID, Gould Inc., Medical Products Division, Oxnard, Calif. 93030), blood sampling, and drug administration. Limb leads are placed subcutaneously for monitoring of lead II ECG. Blood pressure and ECG measurements are recorded (Gould 440 recorder, Gould Inc., Instrument Systems Division, Cleveland, Ohio 44114).

Blood Sampling

Blood samples may be drawn into plastic syringes containing 3.8% trisodium citrate (1:10). Plasma is prepared by centrifugation at 2,000 g-forces for 10 min. Venous blood for in vitro studies is collected from healthy, drug free, male volunteers.

Coagulation Assays, Template Bleeding Time and Hematology

Activated partial thromboplastin time (aPTT) determinations are carried out using the reagents and methods of Dade Diagnostics, Inc. (Aguada, Puerto Rico 0602). Thrombin clotting times are determined by incubating 0.1 ml of rat plasma at 37° C. with 0.1 ml of 0.1M Tris buffer, pH 7.5 for 30 seconds. Coagulation is started with 0.1 ml of bovine thrombin (Sigma Diagnostics, St. Louis, Mo. 63178) solution (12 NIH units/ml). All clotting times are measured semiautomatically using a MLA-Electra 750 automatic coagualation timer, MLA, Inc. (Pleasantville, N.Y. 10570). The concentration required for doubling the clotting time ($ID_2$) is calculated using simple linear regression. Determination of $t_{1/2}$ is calculated for the antithrombin activity (thrombin time) after Peptide 1 (SEQ ID NO: 1) infusion at rates of 1 and 5 nmol/kg/min. Estimation of $t_{1/2}$ is made by linear regression of the response data over time.

Template bleeding times are performed on the median surface of the left leg after the hair has been removed (Nair, Carter-Wallace, Inc., New York, N.Y. 10105) using a Surgicutt® bleeding time device (International Technidyne Corp., Edison, N.J. 08820). Template bleeding times are determined 60 and 30 min before administration of the drug, 15, 30, 60, 120, 180 and 240 min after drug administration.

Whole blood cell counts and analysis of the hemoglobin content are determined on a 140 µL blood sample anticoagulated with EDTA processed with a hematology analyzer (Technicon El, Miles Technicon, Tarrytown, N.Y. 10591). Samples were taken at 60 and 30 min before administration of the drug, 15, 30, 60, 120, 180 and 240 min after drug administration.

Platelet Aggregation Tests

Human platelet-rich plasma (PRP) is prepared by centrifugation at 200 g-forces for 10 min. room temperature. Platelet poor plasma (PPP) is prepared by centrifugation at 2,000 g-forces for 10 min. PRP is exposed only to plastic laboratory ware. All experiments are completed within 3 hours of blood collection. Platelet aggregation is measured photometrically using a Chrono-log dual channel aggregometer (Chrono-log Corp., Haverstown, Pa. 19083). One hundred percent light transmission is defined with autologus PPP. Percent maximal change in light transmission is determined from PRP following addition of ADP (1 µM) or thrombin. Thrombin (0.2–2.0 Units/ml)-induced platelet aggregation is concentration dependent and the half-maximal concentration is used for inhibition studies. Peptide 1 (SEQ ID NO: 1) is incubated with PRP (0.45 ml) for 30 seconds prior to the addition of ADP or thrombin. Aggregation is measured in a total volume of 0.5 ml. Inhibitory responses are expressed as percent inhibition when compared to a control value. The concentration resulting in 50% inhibition of aggregation ($IC_{50}$) is calculated by simple linear regression.

Platelet aggregation in blood is performed in saline diluted (1:2) citrated blood using a whole blood aggregomenter (Chrono-log, model 540-VS). Aliquots of diluted blood are placed in plastic cuvettes and incubated at 37° C. for 15 min. Addition of ADP (2 μM) or thrombin (0.4 U/ml) is used to induce aggregation and the change in electrical impedance is registered on a strip chart recorder. Aggregation is measured in a total blood volume of 1.0 ml. Inhibitory responses are expressed as percent inhibition when compared to a control value. The concentration resulting in 50% inhibition of aggregation ($IC_{50}$) is calculated by simple linear regression.

FeCl$_3$ Arterial Thrombosis Model in Rats (In Vivo)

In Vivo anti-thrombotic effects of Peptide 1 (SEQ ID NO: 1) in rats is also utilized for evaluation. For example, Peptide 1 (SEQ ID NO: 1) is evaluated for antithrombotic activity in a platelet-dependent thrombin mediated FeCl$_3$-induced rat carotid artery thrombosis model according to R. J. Broersma, et al., Thromb. Res. 64, 405–412 (1991), said reference incorporated herein by reference as if fully set forth.

Results

The results from this study show that Peptide 1 (SEQ ID NO: 1), unexpectedly, is much more potent than Peptide 3 (SEQ ID NO: 7), Peptide 4 (SEQ ID NO: 8), or even Peptide 2 (SEQ ID NO: 2) as an inhibitor of thrombin-induced platelet aggregation.

TABLE VII

ANTICOAGULANT ACTIVITY IN HUMAN PLASMA OF PEPTIDE 1 COMPARED WITH PEPTIDES 2, 3 AND 4

| | | $ID_2$, nM* | |
|---|---|---|---|
| Peptide | Peptide Sequence | aPTT | Thrombin Time |
| 3 | fPRPGcGRGD(Nle)PcGDYEPIPE | 998 ± 108 | 141 ± 52 |
| 4 | fPRPGCGRGD(Nle)PCGDYEPIP EEAYD | 115 ± 24 | 14 ± 3 |
| 2 | fPRPGcGRGDFPcGDYEPIPEEA (Cha)e | 60 ± 18 | 24 ± 7 |
| 1 | fPRPGcGRGD(Nle)PcGDYEPIPE EA(Cha)e | 12 ± 0.2 | 5 ± 1 |

*$ID_2$, value (mean ± S.D.) is the concentration necessary for doubling the clotting times (in seconds) from control in triplicate. aPTT, activated partial thromboplastin time.

With reference to Table VII, Peptide 1 (SEQ ID NO: 1) is an analog of Peptide 2 (SEQ ID NO: 2) wherein the phenylalanine (Phe) in the cyclic RGD-X sequence of Peptide 2 (SEQ ID NO: 2) is substituted with norleucine (Nle). Peptide 1 (SEQ. ID NO: 1) is an analog of Peptide 2 (SEQ ID NO: 2) wherein the anion binding exosite associating moiety (portion C) is truncated. Peptide 4 (SEQ ID NO: 8) is an analog of Peptide 1 (SEQ. ID NO: 1) which contains only natural L-amino acids. Whereas Peptides 1 (SEQ ID NO: 1) and 2 (SEQ ID NO: 2) are of this invention, Peptides 3 (SEQ ID NO: 7) and 4 (SEQ ID NO: 8) are not of this invention.

Peptide 1 (SEQ ID NO: 1) doubles ($ID_2$) the aPTT and thrombin time with 12 and 5 nM concentrations, respectively. This corresponds to a fivefold increase in values of anticoagulant activity as compared to Peptide 2 (SEQ ID NO: 2). Table VII illustrates that Peptides 3 (SEQ ID NO: 7) and 4 (SEQ ID NO: 8) have less anticoagulant activity than Peptide 2.

TABLE VIII

INHIBITION OF HUMAN PLATELET AGGREGATION BY PEPTIDE 1 COMPARED WITH PEPTIDES 2, 3 AND 4

| | | $IC_{50}$* | |
|---|---|---|---|
| Peptide | Peptide Sequence | ADP μM | Thrombin nM |
| 3 | fPRPGcGRGD(Nle)PcGDYEPIPE | 29.3 ± 7.8 | 407 ± 372 |
| 4 | fPRPGCGRGD(Nle)PCGDYEPIP EEAYD | 35.9 ± .5 | 408 ± 180 |
| 2 | fPRPGcGRGDFPcGDYEPIPEEA (Cha)e | 18.7 ± 4.6 | 60 ± 26 |
| 1 | fPRPGcGRGD(Nle)PcGDYEPIPEE A(Cha)e | 31.7 ± 2.3 | 0.4 ± 0.08 |

*$IC_{50}$ value (mean ± S.D.) is the concentration necessary to inhibit platelet aggregation in PRP to 50% of the control aggregation in duplicate Thrombin-Induced Platelet Aggregation The dose-dependent inhibition of human platelet aggregation of Peptides 1–4 (SEQ ID NOS: 1, 2, 7 and 8) is illustrated in Table VIII. Thrombin-induced platelet aggregation is most effectively inhibited by Peptide 1 (SEQ ID NO: 1) with an $IC_{50}$ value of 399±76 pM, a 150-fold increase over Peptide 2 (SEQ ID NO: 2) ($IC_{50}$=60±26 nM).

Peptide 4 (SEQ ID NO: 8), the analog with all natural L-amino acids, and Peptide 3 (SEQ ID NO: 7), the analog with the shortened COOH terminus, are approximately 1,000-fold less active than Peptide 1.

ADP-Induced Platelet Aggregation

Disintegrin activity is measured by dose-dependent inhibition of ADP-induced aggregation of human platelets and is illustrated in Table VIII. Peptide 1 (SEQ ID NO: 1) ($IC_{50}$=32 μM) and Peptide 2 (SEQ ID NO: 2) ($IC_{50}$=19 μM) are shown to have similar activity. Peptide 4 (SEQ ID NO: 8), the analog with all natural L-amino acids, and Peptide 3 (SEQ ID NO: 7), the analog with the shortened COOK terminus, are approximately equivalent to Peptide 1 (SEQ ID NO: 1) in disintegrin activity.

Whole Blood Platelet Aggregation

Figure 3:
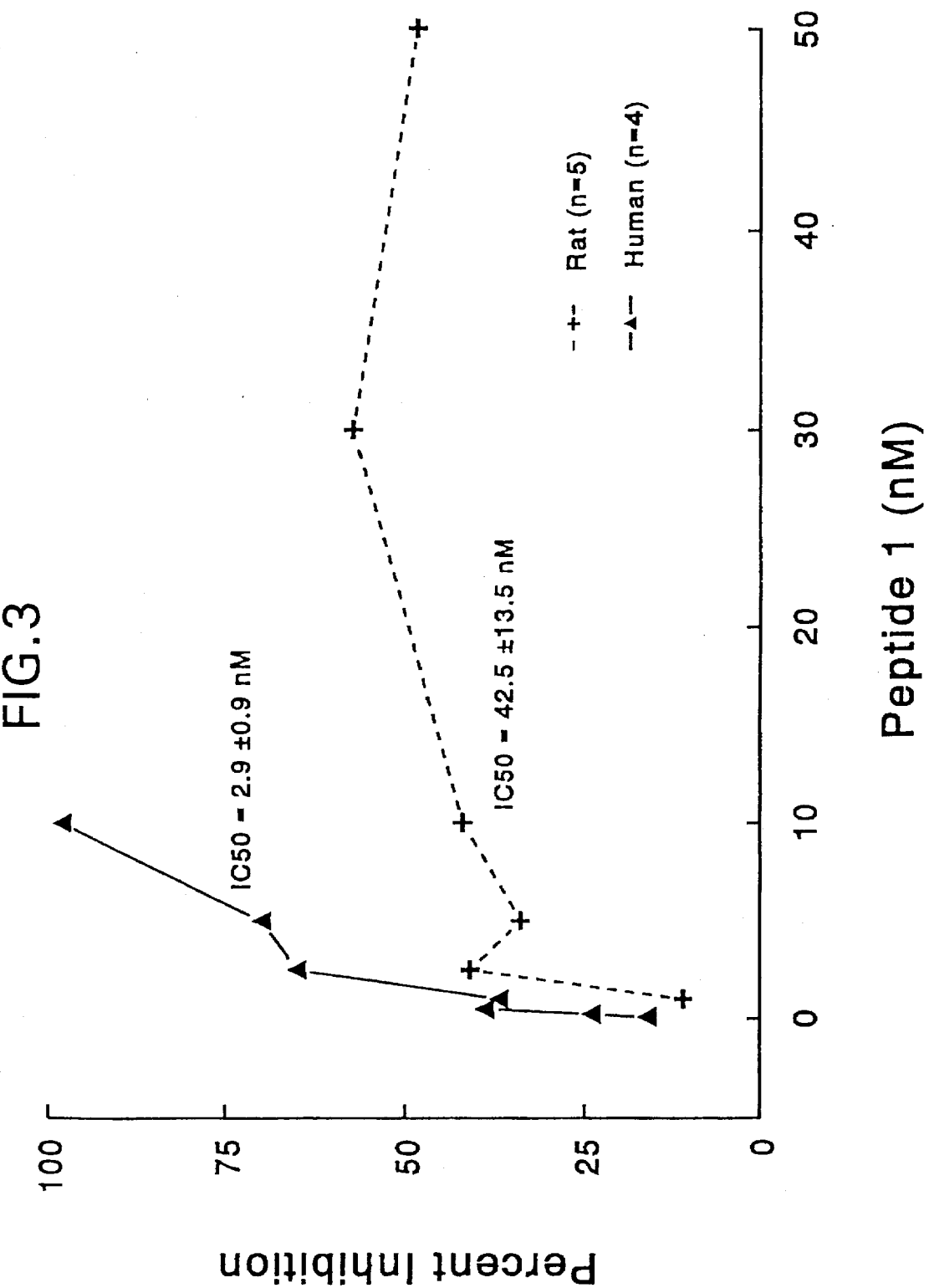
FIG. 3 shows the effect of Peptide 1 on thrombin-amplified whole blood aggregation.(▲) represents human blood samples. (+) represents rat blood samples.

Human and rat whole blood platelet aggregation induced by a combination of ADP (0.5 μM) and thrombin (0.025 U/ml) is inhibited by Peptide 1 with $IC_{50}$ of 2.9 and 42.5 nM, respectively (see FIG. 3). Thus, Peptide 1 (SEQ ID NO: 1) is approximately 15 times more active in human blood as compared to rat blood. Furthermore, Peptide 1 (SEQ ID NO: 1) completely inhibits aggregation in human blood in contrast to a plateau of inhibition in rat blood at approximately 50%.

Intravenous Administration of Peptide 1 in Dogs

Figure 4:
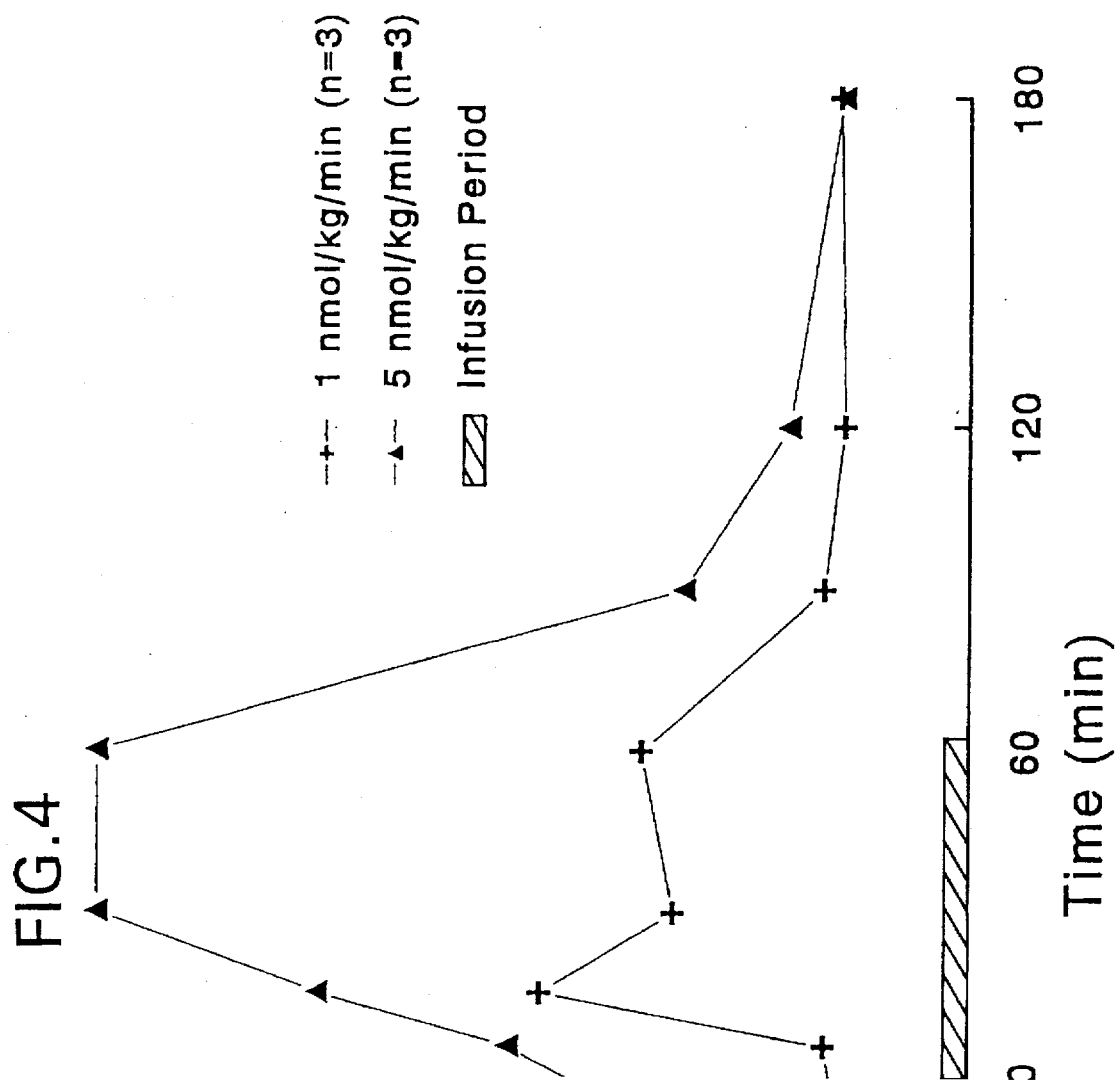
FIG. 4 shows the effect of Peptide 1 infusion on thrombin times in an anesthetized dog.(▲) represents 5 nmol/kg/min rate. (+) represents 1 nmol/kg/min rate. (▬) represents the infusion period.
Figure 5:
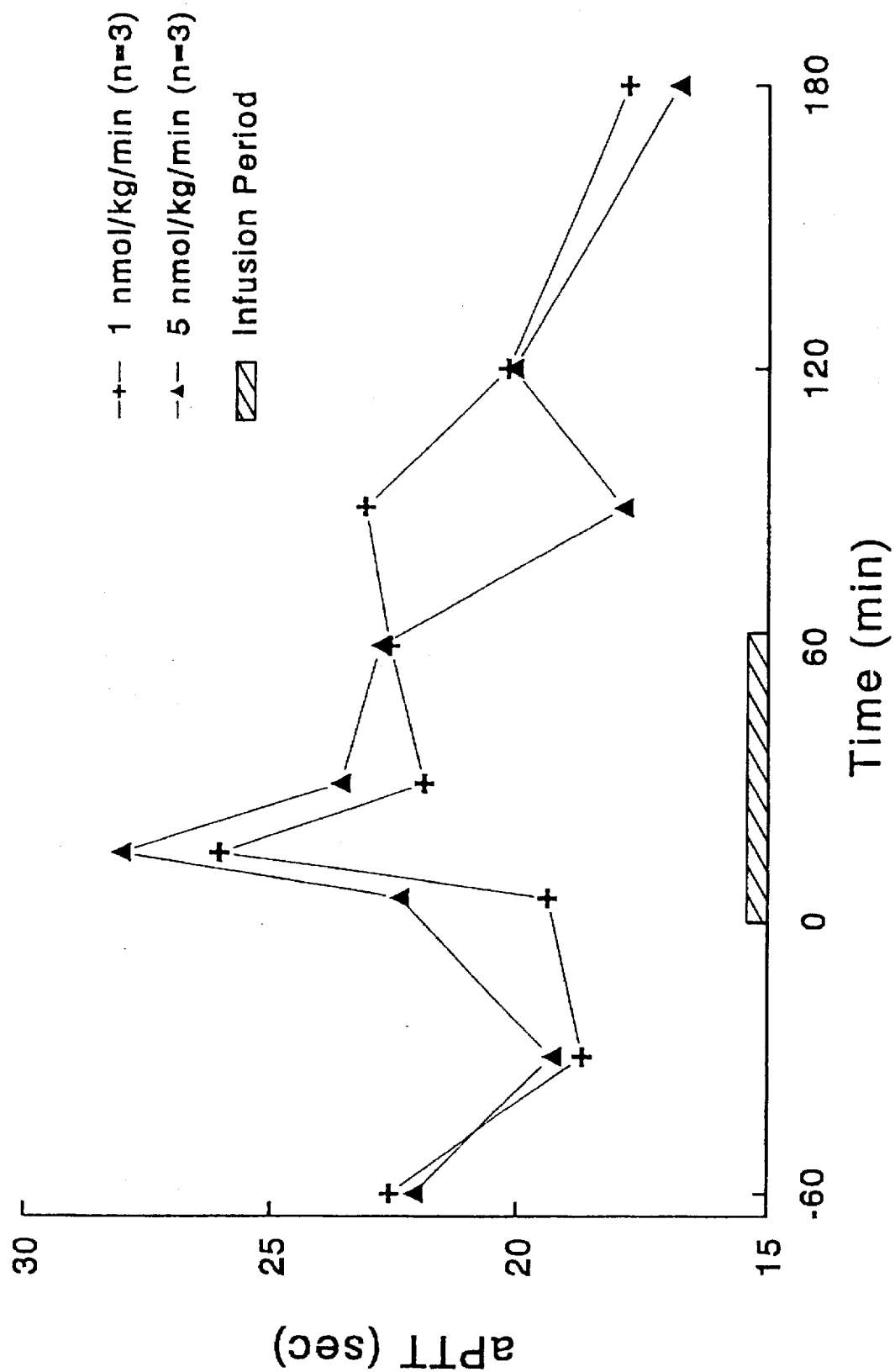
FIG. 5 shows the effect of Peptide 1 on aPTT in an anesthetized dog. (▲) represents a 5 nmol/kg/min rate. (+) represents 1 nmol/kg/min rate. (▬) represents the infusion period.
Figure 6:
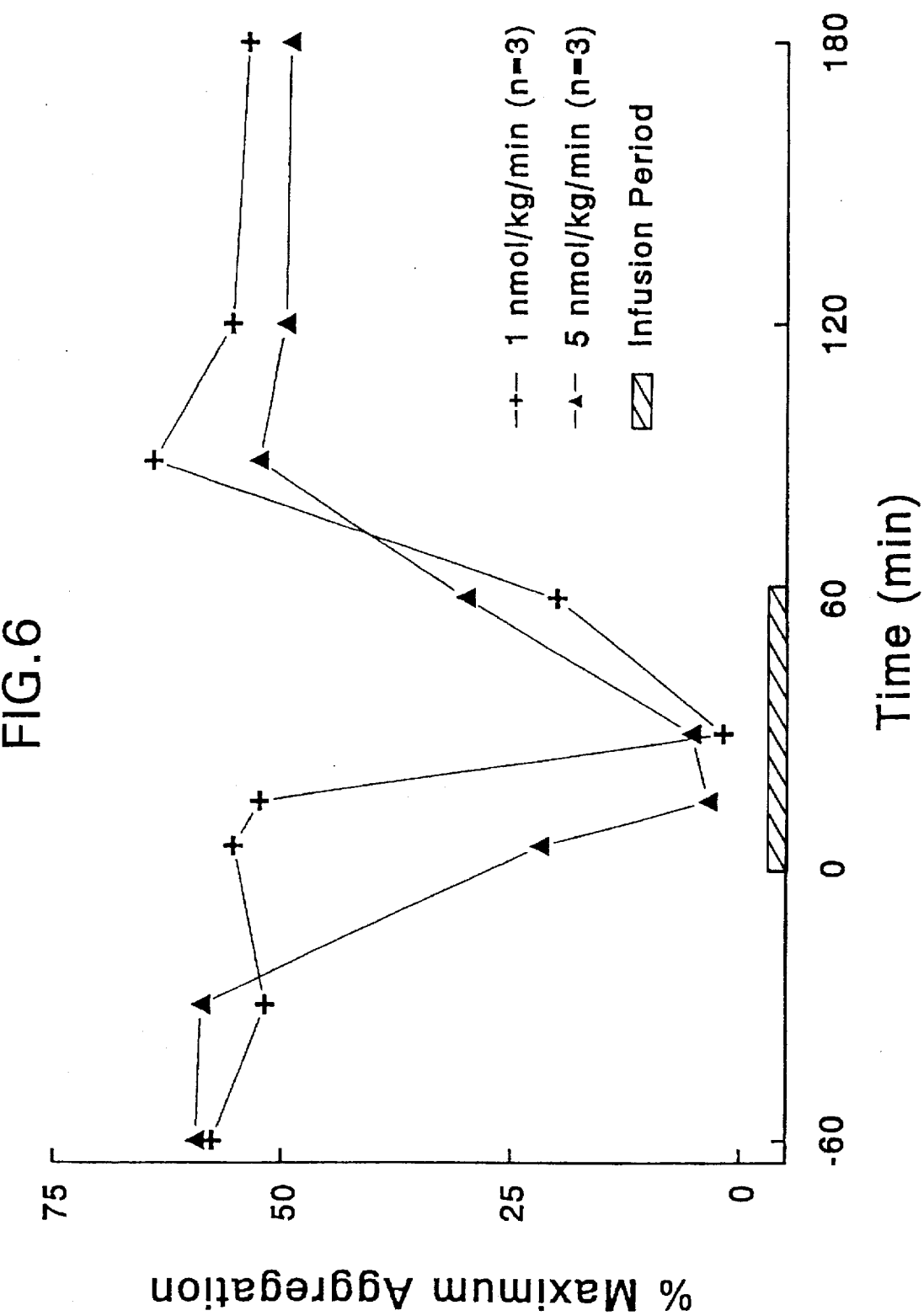
FIG. 6 shows the effect of Peptide 1 infusion on thrombin-platelet aggregation in dogs. (▲) represents a 5 nmol/kg/min rate. (+) represents a 1 nmol/kg/min rate. (▬) represents the infusion period.

Peptide 1 (SEQ ID NO: 1) demonstrates inhibition of thrombin and platelet aggregation when infused for 1 hr in anesthetized dogs. Furthermore, the effect of Peptide 1 (SEQ ID NO: 1) is short duration after the infusion is stopped. Thrombin times (FIG. 4) and aPTT (FIG. 5) are dose-dependently prolonged by infusion rates of 1 and 5 nmol/kg/min. Thrombin times are more sensitive to inhibition by the infusion of Peptide 1 (SEQ ID NO: 1) than are the aPTT assays. The summary data in FIG. 6 illustrates that maximum inhibition is complete Within 15–30 min. After the infusion is stopped (60 min), thrombin activity is restored, with a pharmacodynamic $t_{1/2}$ of 17±0.1 and 26±3.2 min, respectively for infusion of 1 and 5 nmol/kg/min.

Inhibition of platelet aggregation confirms the effect of Peptide 1 (SEQ ID NO: 1) on coagulation tests. Infusion of Peptide 1 (SEQ ID NO: 1) inhibits thrombin-induced platelet aggregation with 15 min (FIG. 6). Inhibition is maintained for the duration of the 1 hr infusion period in 2 out of 3 dogs. Platelet activity is restored, with a pharmacodynamic $t_{1/2}$ of 12.8±1.1 min after the 1 nmol/kg/min infusion is stopped.

Figure 7:
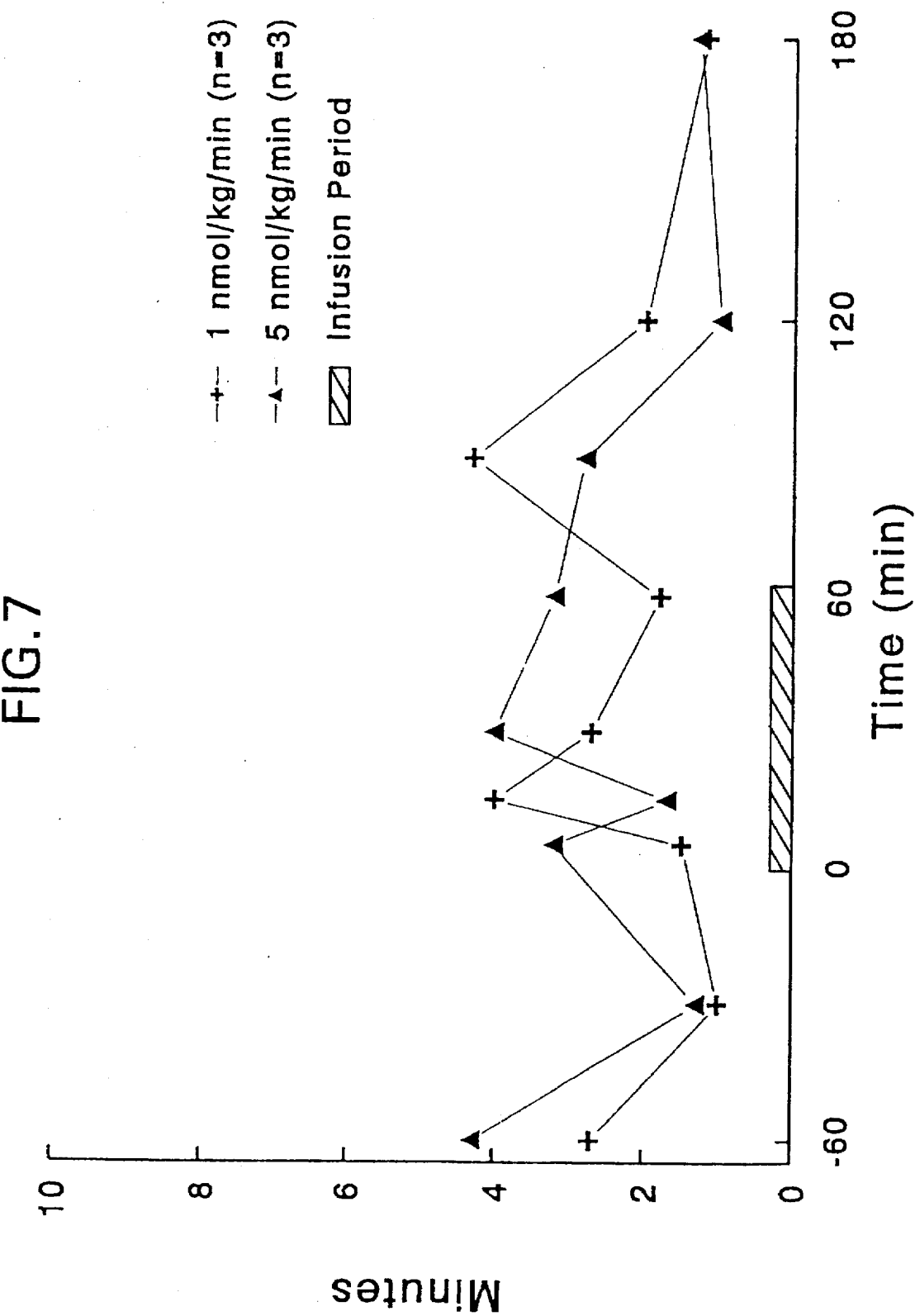
FIG. 7 shows the effect of Peptide 1 on bleeding time in anesthetized dogs. (▲) represents a 5 nmol/kg/min rate. (+) represents a 1 nmol/kg/min rate. (▬) represents the infusion period.
Figure 8:
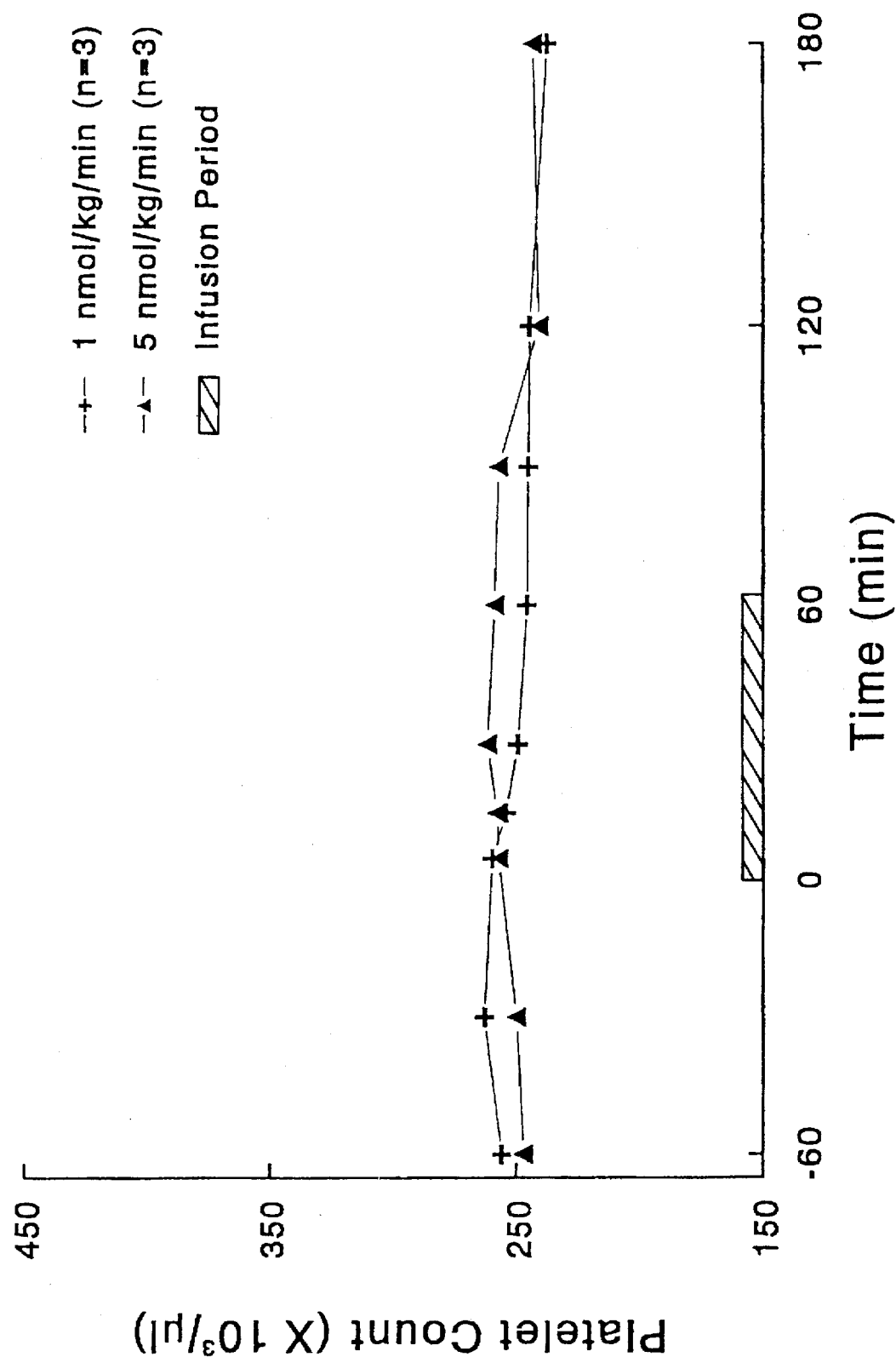
FIG. 8 shows the effect of Peptide 1 infusion on platelet count in anesthetized dogs.(▲) represents a 5 nmol/kg/min rate. (+) represents a 1 nmol/kg/min rate. (▬) represents the infusion period.
Figure 9:
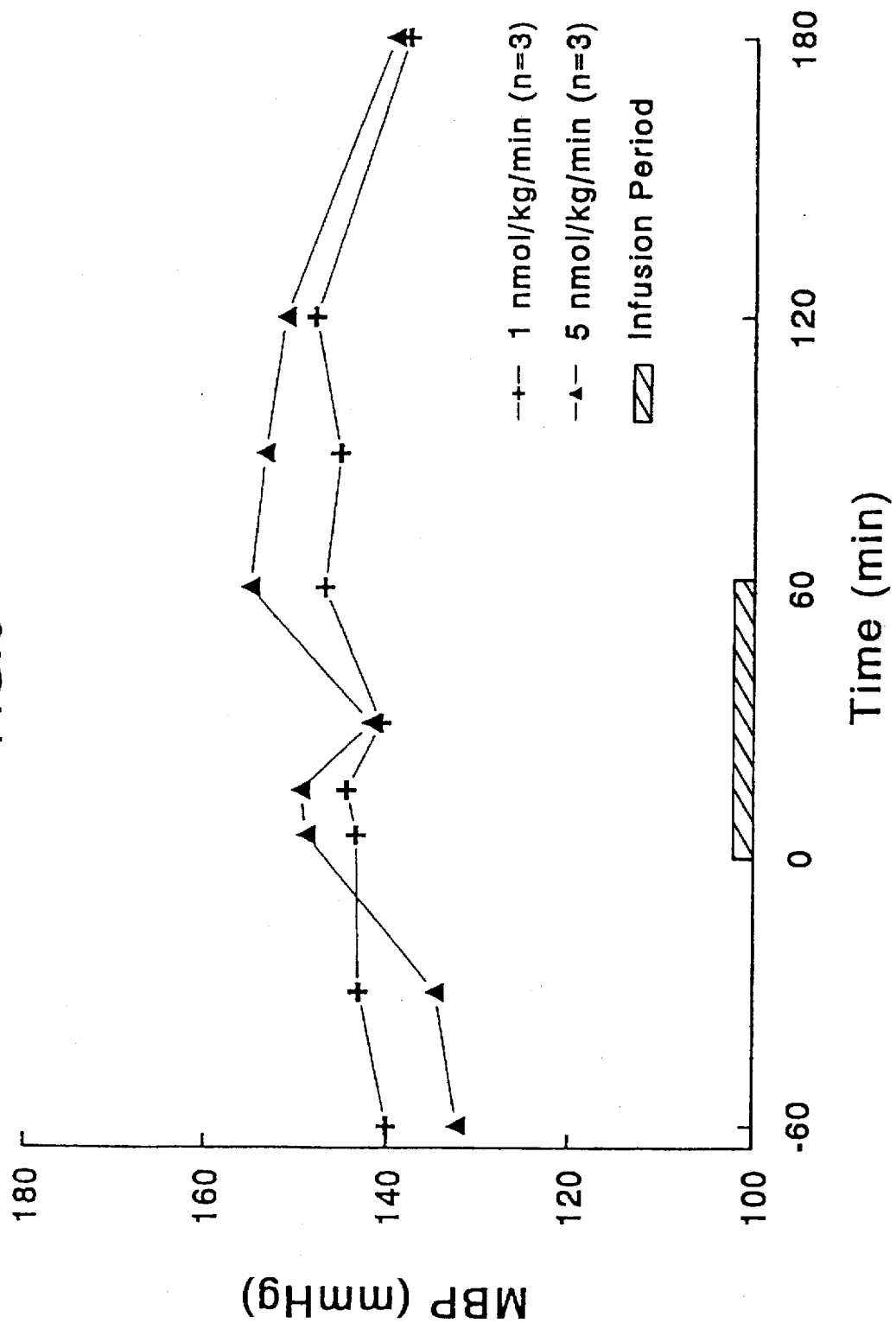
FIG. 9 shows the effect of Peptide 1 on mean blood pressure in anesthetized dogs.(▲) represents a 5 nmol/kg/min rate. (+) represents a 1 nmol/kg/min rate. (▬) represents the infusion period.
Figure 10:
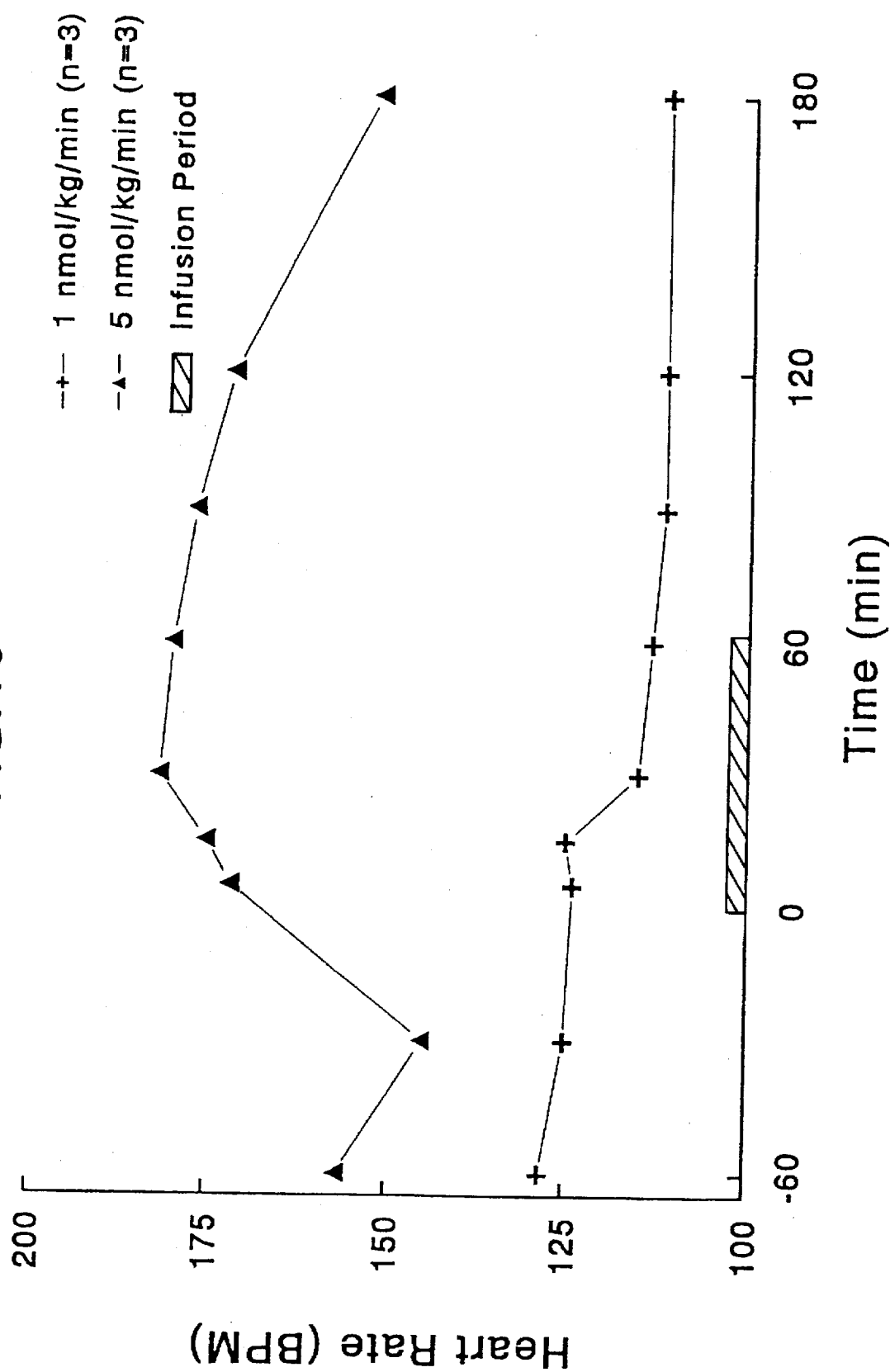
FIG. 10 shows the effect of Peptide 1 infusion on heart rate in anesthetized dogs. (▲) represents a 5 nmol/kg/min rate. (+) represents a 1 nmol/kg/min rate. (▬) represents the infusion period.

ADP-induced platelet aggregation is inhibited in 1 out of 3 dogs at each dose rate. In vitro, ADP-induced platelet aggregation is inhibited at µM levels. It is believed, but this invention is not bound by such belief, that the 1:2 dilution of blood with saline in whole blood platelet aggregation reduces the concentration of Peptide 1 (SEQ ID NO: 1) necessary for effective inhibition of ADP-induced platelet aggregation. The bleeding times (FIG. 7) and platelet counts (FIG. 8) remain stable in dogs receiving Peptide 1 (SEQ ID NO: 1). Blood pressure (FIG. 9) and heart rates (FIG. 10) are modestly elevated in a dose-dependent fashion. These parameters return to baseline control values 2 hr after infusion ends.

TABLE IX

EFFECT OF PEPTIDE 1 ON ARTERIAL THROMBOSIS IN RATS

| PEPTIDE 1 | OCCLUSION TIME | | nANIMALS |
|---|---|---|---|
| nmol/kg/min[a] | CONTROL | TREATED | OCCLUDED/TREATED |
| 5 | 15.7 ± 1.4 | 24.1 ± 5.8 | 6/6 |
| 10 | 17.1 ± 1.3 | 40.4 ± 5.8** | 4/7 |
| 25 | 18.6 ± 1.7 | 58.1 ± 9.5** | 1/5 |

Figure 11:
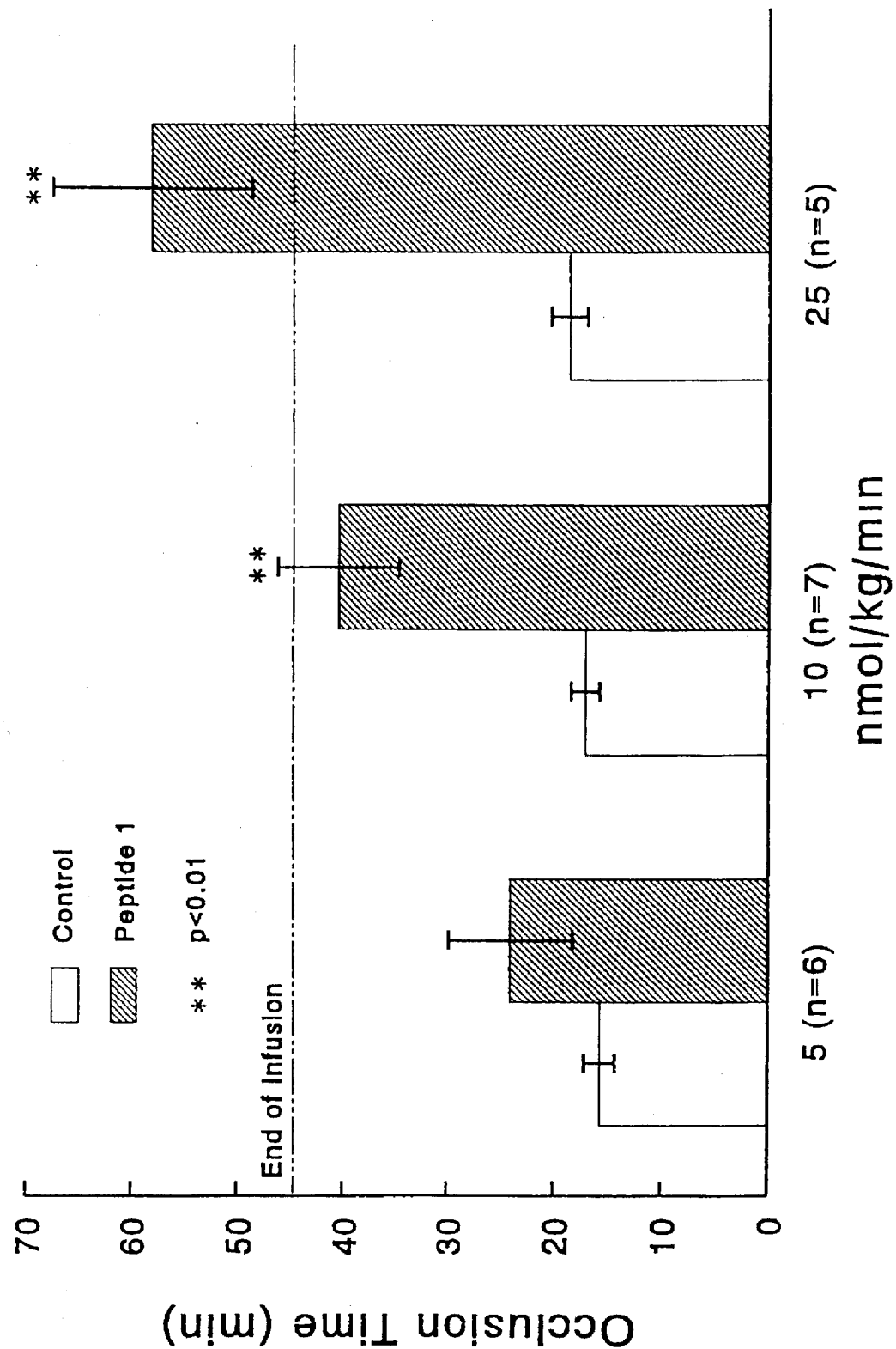
FIG. 11 shows, in bar graph form, the effect of Peptide 1 on FeCl$_3$ arterial occlusion time in rats. The control is represented by the unshaded bars while Peptide 1 is represented by the shaded bars. In this figure, p represents probability, while n represents the number of animals tested.

[a]Infused over 60 min beginning 15 min before FeCl$_3$ injury.
**p < 0.01 vs control Peptide 1 (SEQ ID NO: 1) is evaluated for antithrombotic activity in the FeCl$_3$-induced rat carotid artery thrombosis model. Thrombotic occlusion is dose-dependently prolonged by continuous intravenous infusion for 1 hr beginning 15 min before application of FeCl$_3$ at dose rates of 5, 10 and 25 nmol/kg/min (see Table IX and FIG. 11). Occlusion is prevented during infusion in 4 of 5 rats at a dose rate of 25 nmol/kg/min. At rates of 10 and 5 nmol/kg/min, occlusion is prevented in 4 of 7 and 0 of 6 rats, respectively. The dose rate of Peptide 1 (SEQ ID NO: 1) required to double the occlusion time after FeCl$_3$ application is 19.3 nmol/kg/min compared to 33.7 nmol/kg/min previously observed for Peptide 2 (SEQ ID NO: 2).

TABLE X

INHIBITION OF HUMAN PLATELET AGGREGATION: "(L)CYS LOOP" VS. "(D)CYS LOOP"

| | | IC$_{50}$[a] | |
|---|---|---|---|
| Peptide | Peptide Sequence | ADP µM | Thrombin nM |
| 5 | fPRPGCRIPRGD(Nle)PADC GDYEPIPEEA(Cha)e | 1.4 ± 0.3 | 231 ± 181 |
| 6 | fPRPGcRIPRGD(Nle)PADc GDYEPIPEEA(Cha)e | 2.1 ± 0.4 | 21 ± 20 |

[a]IC$_{50}$, value (mean ± S.D.) is the concentration necessary to inhibit platelet aggregation in PRP to 50% of the control aggregation in triplicate Table X illustrates the difference between the two stereoisomers that result from the substitution of (D)Cys with (L)Cys residues in the connecting "bridge" between the catalytic site inhibitor and the anion-binding exosite recognition sequence. Peptides 5 (SEQ ID NO: 9) and 6 (SEQ ID NO: 10) represent analogs of Peptide 1 (SEQ ID NO: 1) which contain additional residues in the cyclic RGD sequence. Peptide 5 (SEQ ID NO: 9) also differs in that it possesses (L)Cys residues in the connecting "bridge" as opposed to the (D)Cys. The different spatial orientation conferred on the cyclic RGD sequence results in greater inhibition of thrombin-induced platelet aggregation of human platelets by the (D)Cys analog, Peptide 6 (SEQ ID NO: 10). A 10-fold difference in thrombin activity is noted between the two stereoisomers. There are, however, no differences on inhibition of ADP-induced platelet aggregation and anticoagulant activity. Note that modification of Peptide 1 (SEQ ID NO: 1) to produce an analog containing only natural L-amino acids—Peptide 4 (SEQ ID NO: 8)—amplifies the difference between the two stereoisomers. Indeed, Peptide 1 (SEQ ID NO: 1) has approximately 1,000-fold greater inhibition if thrombin-induced platelet aggregation than Peptide 4 (SEQ ID NO: 8) (see Table VIII). There is no difference between these two stereoisomers on inhibition of ADP-induced platelet aggregation. Anticoagulant activity, however, is greater for the (D)Cys containing analog—Peptide 1 (SEQ ID NO: 1)—than the all natural amino acid analog—Peptide 4 (SEQ ID NO: 8).

Relative Activity of Peptide 1 vs. Analogs of Peptide 1

Tables XI–XIV illustrate the ratios of analogs of Peptide 1 (SEQ ID NO: 1) versus established IC$_{50}$ platelet inhibition and ID$_2$ anticoagulation data. For the purposes of these comparisons, the Peptide 1 (SEQ ID NO: 1) sample has the following activity: coagulation—ID$_2$ (aPTT=27.9 nM; Thrombin Time=15 nM); aggregation—IC$_{50}$ (Thrombin= 5.8 nM; ADP=11.4 µM). The values for aPTT, Thrombin Time, Thrombin and ADP for Peptides 7–18 (SEQ ID NOS: 11–22) in Tables XI–XIV represent only comparative values and are not intended to represent actual concentrations of peptides—hence, no units are provided. For example, an aPTT value of 0.99 for Peptide 7 (SEQ ID NO: 11) signifies that Peptide 7 (SEQ ID NO: 11) is 99% as active as Peptide 1 (SEQ ID NO: 1) in assays of the activated partial thromboplastin time (aPTT) in normal human plasma.

TABLE XI

RELATIVE ACTIVITY: PEPTIDE 1 VS. $B_4$-SUBSTITUTED ANALOGS

| Pepide | Peptide Sequence | Coagulation | | Aggregation | |
|---|---|---|---|---|---|
| | | aPTT | Thrombin Time | Thrombin | ADP |
| 7 | fPRPGcGRGDMPcGDYEPIPEEA(Cha)e | 0.99 | 0.19 | 0.10 | 0.74 |
| 8 | fPRPGcGRGD(Cha)PcGDYEPIPEEA(Cha)e | 0.60 | 1.04 | 0.12 | 0.43 |

Table XI illustrates the differences between two analogs of Peptide 1 (SEQ ID NO: 1)—peptides 7 (SEQ ID NO: 11) and 8 (SEQ ID NO: 12), which are both compounds of this invention. Peptide 7 (SEQ ID NO: 11) is an analog of Peptide 1 (SEQ ID NO: 1) in which the Nle at the $B_4$ moiety has been replaced with Met and Peptide 8 (SEQ ID NO: 12) is an analog of Peptide 1 (SEQ ID NO: 1) in which the Nle at the $B_4$ moiety has been replaced with Cha. Peptide 8 (SEQ ID NO: 12) is about ⅓ less active than Peptide 1 (SEQ ID NO: 1) in assays of the aPTT, but the aPTT value Peptide 7 (SEQ IS NO: 11) is essentially the same as that of Peptide 1 (SEQ ID NO: 1). As for the thrombin time values, these values vary with each peptide—Peptide 7 (SEQ ID NO: 11) being only 19% as active as Peptide 1 (SEQ ID NO: 1), whereas peptide 8 (SEQ ID NO: 12) is actually more active than Peptide 1 (SEQ ID NO: 1). A 10-fold difference in thrombin activity is noted between Peptide 1 (SEQ ID NO: 1) and either of the analogs. As for ADP activity, Peptide 8 (SEQ ID NO: 12) is roughly ½ as effective as Peptide 1 (SEQ ID NO: 1) whereas Peptide 7 (SEQ ID NO: 11) is about ¾ as effective as Peptide 1 (SEQ ID NO: 1).

TABLE XII

RELATIVE ACTIVITY: PEPTIDE 1 VS. $B_3$-SUBSTITUTED PENICILLAMINE ANALOGS

| Peptide | Peptide Sequence | Coagulation | | Aggregation | |
|---|---|---|---|---|---|
| | | aPTT | Thrombin Time | Thrombin | ADP |
| 9 | fPRPGcGRGD(Nle)P(D-Pen)GDYEPIPEEA(Cha)e | 0.11 | 0.15 | 0.06 | 0.13 |
| 10 | fPRPGcG(Me-R)GD(Nle)P(D-Pen)GDYEPIPEEA(Cha)e | 0.52 | 0.92 | 0.08 | 6.0 |

Table XII illustrates the differences between two penicillamine analogs of Peptide 1 (SEQ ID NO: 1)—Peptides 9 (SEQ ID NO: 13) and 10 (SEQ ID NO: 14), neither of which are peptides of this invention. This table is submitted to show the interchangeability of the Arg at the $B_3$ moiety with Me-Arg. The introduction of the penicillamine moiety greatly decreases the activity of Peptide 9 (SEQ ID NO: 13) in all categories. As for Peptide 10 (SEQ ID NO: 14), the same decrease is noted in thrombin activity is noted as in Peptide 9 (SEQ ID NO: 13). However, there is only a slight decrease in thrombin time whereas the ADP activity increased six fold as compared to Peptide 1 (SEQ ID NO: 1).

TABLE XIII

RELATIVE ACTIVITY: PEPTIDE 1 VS. $B_2$-SUBSTITUTED ANALOGS

| Pepide | Peptide Sequence | Coagulation | | Aggregation | |
|---|---|---|---|---|---|
| | | aPTT | Thrombin Time | Thrombin | ADP |
| 11 | fPRPGcvRGD(Nle)PcGDYEPIPEEA(Cha)e | 0.37 | 0.86 | 0.13 | 0.18 |
| 12 | fPRPGcyRGD(Nle)PcGDYEPIPEEA(Cha)e | 0.53 | 1.38 | 0.14 | 0.18 |
| 13 | fPRPGcRGD(Nle)PcGDYEPIPEEA(Cha)e | 0.40 | 0.27 | 0.04 | 0.20 |
| 14 | fPRPGctRGD(Nle)PcGDYEPIPEEA(Cha)e | 0.75 | 0.93 | 0.18 | 0.22 |
| 15 | fPRPGcpRGD(Nle)PcGDYEPIPEEA(Cha)e | 0.59 | 1.12 | 0.36 | 0.26 |

Table XIII illustrates the interchangeability of the Gly residue at $B_2$ with various D-amino acid residues. Peptides 11 (SEQ ID NO: 15), 12 (SEQ ID NO: 16), 14 (SEQ ID NO: 18) and 15 (SEQ ID NO: 19) are analogs of Peptide 1 (SEQ ID NO: 1) in which the $B_2$ moiety has been substituted with various D-amino acids and are peptides of this invention. Peptide 13 (SEQ ID NO: 17), which is not a peptide of this invention, is an analog of Peptide 1 (SEQ ID NO: 1) in which the Gly residue at $B_2$ is deleted.

TABLE XIV

RELATIVE ACTIVITY: PEPTIDE 1 VS. $A_1$-SUBSTITUTED ANALOGS

| Peptide | Peptide Sequence | Coagulation | | Aggregation | |
|---|---|---|---|---|---|
| | | aPTT | Thrombin Time | Thrombin | ADP |
| 16 | (D-Phg)PRPGcGRGD(Nle)PcGDYEPIPEEA(Cha)e | 0.72 | 1.03 | 0.94 | 0.54 |
| 17 | (D-3-Tiq)PRPGcGRGD(Nle)PcGDYEPIPEEA(Cha)e | 0.62 | 0.93 | 0.13 | 1.27 |
| 18 | (N-Me-f)PRPGcGRGD(Nle)PcGDYEPIPEEA(Cha)e | 1.73 | 0.77 | 0.55 | 0.43 |

Table XIV illustrates the interchangeability of the (D)Phe residue at the $A_1$ moiety. Peptides 16–18 (SEQ ID NOS: 20–22) are all peptides of this invention. Peptide 16 (SEQ ID NO: 20) exhibits essentially the same thrombin activity and thrombin time as Peptide 1 (SEQ ID NO: 1). Peptide 17 (SEQ ID NO: 21) exhibits essentially the same thrombin time value as Peptide 1 (SEQ ID NO: 1) and has a greater ADP value, but is 10-fold less active in its thrombin value. In comparison, Peptide 18 (SEQ ID NO: 22) exhibits a noticeable increase in aPTT values as compared to Peptide 1 (SEQ ID NO: 1), but exhibits a thrombin time only 77% as active as Peptide 1 (SEQ ID NO: 1) while the thrombin and the ADP values are only half as active as those for Peptide 1 (SEQ ID NO: 1).

What is claimed is:

1. A compound of the formula

X—A—B—C—Y    (1)

wherein

X is hydrogen, acetyl, or a t-butyloxy carbonyl group;
A is a peptide analog of the formula $A_1$—$A_2$—$A_3$    (2)

wherein $A_1$ is (D)Phe, (D)Phg, (D)3-Tiq, N-Me-(D)Phe;
$A_2$ is Pro;
$A_3$ is Arg;

B is a peptide analog of the formulae

Pro—$B_1$—(D)Cys'—$B_2$—$B_3$—Gly—Asp—$B_4$—Pro—(D)Cys'—$B_1$    (3)
    |                                                              |
    S————————————————————S or

Pro—$B_1$—    (4)

—(D)Cys'—$B_2$—$B_3$—Gly—Asp—Nle—Pro—Ala—Asp—(D)Cys'—$B_1$
  |                                                                |
  S————————————————————————S wherein $B_1$ is Gly;
$B_2$ is Gly, (D)Tyr, (D)Val, (D)Thr or (D)Pro;
$B_2'$ is Arg-Ile-Pro;
$B_3$ is Arg;
$B_4$ is Nle or Phe;

C is a peptide analog of the formula

Asp—$C_1$—$C_2$—$C_3$—$C_4$—$C_5$—$C_6$—$C_7$—$C_8$—$C_9$    (5)

wherein $C_1$ is Tyr;
$C_2$ is Glu;
$C_3$ is Pro;
$C_4$ is Ile;
$C_5$ is Pro;
$C_6$ is Glu;
$C_7$ is Glu;
$C_8$ is Ala-Cha;
$C_9$ is (D)Glu; and
Y is OH or $C_1$–$C_6$ alkoxy;

or a pharmaceutically acceptable salt thereof.

2. A compound of claim 1 wherein said compound is a compound of the formula (SEQ ID NO: 1)

(D)Phe—Pro—Arg—Pro—Gly—(D)Cys'—Gly—Arg—Gly—Asp
                                            S—S          |
Pro—Ile—Pro—Glu—Tyr—Asp—Gly—(D)Cys'—Pro—Nle
|
Glu—Glu—Ala—Cha—(D)Glu—OH

3. A compound of claim 1 wherein said compound is a compound of the formula (SEQ ID NO: 2)

(D)Phe—Pro—Arg—Pro—Gly—(D)Cys'—Gly—Arg—Gly—Asp
                                            S—S          |
Pro—Ile—Pro—Glu—Tyr—Asp—Gly—(D)Cys'—Pro—Phe
|
Glu—Glu—Ala—Cha—(D)Glu—OH

4. A compound of claim 1 wherein said compound is a compound of the formula (SEQ ID NO: 3)

(D)Phg—Pro—Arg—Pro—Gly—(D)Cys'—Gly—Arg—Gly—Asp
                                            S—S          |
Pro—Ile—Pro—Glu—Tyr—Asp—Gly—(D)Cys'—Pro—Nle
|
Glu—Glu—Ala—Cha—(D)Glu—OH

5. A compound of claim 1 wherein said compound is a compound of the formula (SEQ ID NO: 10)

(D)Phe—Pro—Arg—Pro—Gly—(D)Cys'—Arg—Ile—Pro—Arg
                                    S—S            |
Tyr—Asp—Gly—(D)Cys'—Asp—Ala—Pro—Nle—Asp—Gly
|
Glu—Pro—Ile—Pro—Glu—Glu—Ala—Cha—(D)Glu—OH .

6. A method for treating a venous or arterial thrombotic condition in a patient suffering therefrom which comprises administering a therapeutically effective amount of a compound of claim 1.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa at location 1 is phenylalanine in the D-configuration"

( i x ) FEATURE:
        ( A ) NAME/KEY: Modified-site
        ( B ) LOCATION: 6
        ( D ) OTHER INFORMATION: /note= "Xaa at location 6 is D-Cys and is sulfide bonded to D-Cys at location 13"

( i x ) FEATURE:
        ( A ) NAME/KEY: Modified-site
        ( B ) LOCATION: 11
        ( D ) OTHER INFORMATION: /note= "Xaa at location 11 is norleucine"

( i x ) FEATURE:
        ( A ) NAME/KEY: Modified-site
        ( B ) LOCATION: 13
        ( D ) OTHER INFORMATION: /note= "Xaa at location 13 is D-Cys and is sulfide bonded to D-cys at location 6"

( i x ) FEATURE:
        ( A ) NAME/KEY: Modified-site
        ( B ) LOCATION: 24
        ( D ) OTHER INFORMATION: /note= "Xaa at location 24 is cyclohexylalanine"

( i x ) FEATURE:
        ( A ) NAME/KEY: Modified-site
        ( B ) LOCATION: 25
        ( D ) OTHER INFORMATION: /note= "Xaa at location 25 is glutamic acid in the D-configuration"

( x i ) SEQUENCE DESCRIPTION: SEQ ID NO:1:

```
Xaa  Pro  Arg  Pro  Gly  Xaa  Gly  Arg  Gly  Asp  Xaa  Pro  Xaa  Gly  Asp  Tyr
1                   5                        10                      15
Glu  Pro  Ile  Pro  Glu  Glu  Ala  Xaa  Xaa
               20                   25
```

( 2 ) INFORMATION FOR SEQ ID NO:2:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site

```
        ( B ) LOCATION: 1
        ( D ) OTHER INFORMATION: /note= "Xaa at location 1 is
              phenylalanine in the D-configuration"

( i x ) FEATURE:
        ( A ) NAME/KEY: Modified-site
        ( B ) LOCATION: 6
        ( D ) OTHER INFORMATION: /note= "Xaa at location 6 is D-Cys
              and is sulfide bonded to D-Cys at location 13"

( i x ) FEATURE:
        ( A ) NAME/KEY: Modified-site
        ( B ) LOCATION: 13
        ( D ) OTHER INFORMATION: /note= "Xaa at location 13 is D-Cys
              and is sulfide bonded to D-Cys at location 6"

( i x ) FEATURE:
        ( A ) NAME/KEY: Modified-site
        ( B ) LOCATION: 24
        ( D ) OTHER INFORMATION: /note= "Xaa at location 24 is
              cyclohexylalanine"

( i x ) FEATURE:
        ( A ) NAME/KEY: Modified-site
        ( B ) LOCATION: 25
        ( D ) OTHER INFORMATION: /note= "Xaa at location 25 is
              glutamic acid in the D-configuration"

( x i ) SEQUENCE DESCRIPTION: SEQ ID NO:2:

Xaa  Pro  Arg  Pro  Gly  Xaa  Gly  Arg  Gly  Asp  Phe  Pro  Xaa  Gly  Asp  Tyr
1                    5                              10                            15

Glu  Pro  Ile  Pro  Glu  Glu  Ala  Xaa  Xaa
              20                        25
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa at location 1 is D-Cys
            and is sulfide bonded to D-Cys at location 8"

( i x ) FEATURE:
        ( A ) NAME/KEY: Modified-site
        ( B ) LOCATION: 8
        ( D ) OTHER INFORMATION: /note= "Xaa at position 8 is D-Cys
            and is sulfide bonded to D-Cys at location 1"

( x i ) SEQUENCE DESCRIPTION: SEQ ID NO:3:

```
Xaa  Gly  Arg  Gly  Asp  Phe  Pro  Xaa
1                    5
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1
        ( D ) OTHER INFORMATION: /note= "Xaa at location 1 is Tyr
            substituted with a succinyl group"

( i x ) FEATURE:

(A) NAME/KEY: Modified-site
(B) LOCATION: 9
(D) OTHER INFORMATION: /note= "Xaa at location 9 is
cyclohexylalanine"

(ix) FEATURE:
(A) NAME/KEY: Modified-site
(B) LOCATION: 10
(D) OTHER INFORMATION: /note= "Xaa at location 10 is
glutamic acid in the D-configuration"

(xi) SEQUENCE DESCRIPTION: SEQ ID NO:4:

Xaa Glu Pro Ile Pro Glu Glu Ala Xaa Xaa
1               5                   10

(2) INFORMATION FOR SEQ ID NO:5:

(i) SEQUENCE CHARACTERISTICS:
(A) LENGTH: 5 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration"

(xi) SEQUENCE DESCRIPTION: SEQ ID NO:5:

Xaa Pro Arg Pro Gly
1               5

(2) INFORMATION FOR SEQ ID NO:6:

(i) SEQUENCE CHARACTERISTICS:
(A) LENGTH: 3 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration and
substituted with a methyl group"

(xi) SEQUENCE DESCRIPTION: SEQ ID NO:6:

Xaa Pro Arg
1

(2) INFORMATION FOR SEQ ID NO:7:

(i) SEQUENCE CHARACTERISTICS:
(A) LENGTH: 21 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration"

(ix) FEATURE:
(A) NAME/KEY: Modified-site
(B) LOCATION: 6
(D) OTHER INFORMATION: /note= "Xaa at location 6 is D-Cys
and is sulfide bonded to D-Cys at location 13"

(ix) FEATURE:
    (A) NAME/KEY: Modified-site
    (B) LOCATION: 11
    (D) OTHER INFORMATION: /note= "Xaa at location 11 is
        norleucine"

(ix) FEATURE:
    (A) NAME/KEY: Modified-site
    (B) LOCATION: 13
    (D) OTHER INFORMATION: /note= "Xaa at location 13 is D-Cys
        and is sulfide bonded to D-Cys at location 6"

(xi) SEQUENCE DESCRIPTION: SEQ ID NO:7:

Xaa Pro Arg Pro Gly Xaa Gly Arg Gly Asp Xaa Pro Xaa Gly Asp Tyr
1               5                   10                  15

Glu Pro Ile Pro Glu
            20

(2) INFORMATION FOR SEQ ID NO:8:

(i) SEQUENCE CHARACTERISTICS:
       (A) LENGTH: 25 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Xaa at location 1 is
           phenylalanine in the D-configuration"

(ix) FEATURE:
       (A) NAME/KEY: Modified-site
       (B) LOCATION: 11
       (D) OTHER INFORMATION: /note= "Xaa at location 11 is
           norleucine"

(xi) SEQUENCE DESCRIPTION: SEQ ID NO:8:

Xaa Pro Arg Pro Gly Cys Gly Arg Gly Asp Xaa Pro Cys Gly Asp Tyr
1               5                   10                  15

Glu Pro Ile Pro Glu Glu Ala Tyr Asp
            20                  25

(2) INFORMATION FOR SEQ ID NO:9:

(i) SEQUENCE CHARACTERISTICS:
       (A) LENGTH: 29 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Xaa at location 1 is
           phenylalanine in the D-configuration"

(ix) FEATURE:
       (A) NAME/KEY: Modified-site
       (B) LOCATION: 13
       (D) OTHER INFORMATION: /note= "Xaa at location 13 is
           norleucine"

(ix) FEATURE:
       (A) NAME/KEY: Modified-site
       (B) LOCATION: 28
       (D) OTHER INFORMATION: /note= "Xaa at location 28 is
           cyclohexylalanine"

(ix) FEATURE:

(A) NAME/KEY: Modified-site
(B) LOCATION: 29
(D) OTHER INFORMATION: /note= "Xaa at loction 29 is
glutamic acid in the D-configuration"

(xi) SEQUENCE DESCRIPTION: SEQ ID NO:9:

Xaa Pro Arg Pro Gly Cys Arg Ile Pro Arg Gly Asp Xaa Pro Ala Asp
1               5                   10                  15

Cys Gly Asp Tyr Glu Pro Ile Pro Glu Glu Ala Xaa Xaa
            20              25

(2) INFORMATION FOR SEQ ID NO:10:

(i) SEQUENCE CHARACTERISTICS:
(A) LENGTH: 29 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration"

(ix) FEATURE:
(A) NAME/KEY: Modified-site
(B) LOCATION: 6
(D) OTHER INFORMATION: /note= "Xaa at location 6 is D-Cys
sulfide bonded to D-Cys at location 17"

(ix) FEATURE:
(A) NAME/KEY: Modified-site
(B) LOCATION: 13
(D) OTHER INFORMATION: /note= "Xaa at location 13 is
norleucine"

(ix) FEATURE:
(A) NAME/KEY: Modified-site
(B) LOCATION: 17
(D) OTHER INFORMATION: /note= "Xaa at location 17 is D-Cys
and is sulfide bonded to D-Cys at location 6"

(ix) FEATURE:
(A) NAME/KEY: Modified-site
(B) LOCATION: 28
(D) OTHER INFORMATION: /note= "Xaa at location 28 is
cyclohexylalanine"

(ix) FEATURE:
(A) NAME/KEY: Modified-site
(B) LOCATION: 29
(D) OTHER INFORMATION: /note= "Xaa at location 29 is
glutamic acid in the D-configuration"

(xi) SEQUENCE DESCRIPTION: SEQ ID NO:10:

Xaa Pro Arg Pro Gly Xaa Arg Ile Pro Arg Gly Asp Xaa Pro Ala Asp
1               5                   10                  15

Xaa Gly Asp Tyr Glu Pro Ile Pro Glu Glu Ala Xaa Xaa
            20              25

(2) INFORMATION FOR SEQ ID NO:11:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1

-continued ( D ) OTHER INFORMATION: /note= "Xaa at location 1 is
                phenylalanine in the D-configuration"

( i x ) FEATURE:
          ( A ) NAME/KEY: Modified-site
          ( B ) LOCATION: 6
          ( D ) OTHER INFORMATION: /note= "Xaa at location 6 is D-Cys
                and is sulfide bonded to D-Cys at location 13"

( i x ) FEATURE:
          ( A ) NAME/KEY: Modified-site
          ( B ) LOCATION: 13
          ( D ) OTHER INFORMATION: /note= "Xaa at location 13 is D-Cys
                and is sulfide bonded to D-Cys at location 6 "

( i x ) FEATURE:
          ( A ) NAME/KEY: Modified-site
          ( B ) LOCATION: 24
          ( D ) OTHER INFORMATION: /note= "Xaa at location 24 is
                cyclohexylalanine"

( i x ) FEATURE:
          ( A ) NAME/KEY: Modified-site
          ( B ) LOCATION: 25
          ( D ) OTHER INFORMATION: /note= "Xaa at location 25 is
                glutamic acid in the D-configuration"

( x i ) SEQUENCE DESCRIPTION: SEQ ID NO:11:

Xaa  Pro  Arg  Pro  Gly  Xaa  Gly  Arg  Gly  Asp  Met  Pro  Xaa  Gly  Asp  Tyr
1                   5                        10                       15

Glu  Pro  Ile  Pro  Glu  Glu  Ala  Xaa  Xaa
              20                   25

( 2 ) INFORMATION FOR SEQ ID NO:12:

( i ) SEQUENCE CHARACTERISTICS:
          ( A ) LENGTH: 25 amino acids
          ( B ) TYPE: amino acid
          ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /note= "Xaa at location 1 is
                phenylalanine in the D-configuration"

( i x ) FEATURE:
          ( A ) NAME/KEY: Modified-site
          ( B ) LOCATION: 6
          ( D ) OTHER INFORMATION: /note= "Xaa at location 6 is D-Cys
                and is sulfide bonded to D-Cys at location 13"

( i x ) FEATURE:
          ( A ) NAME/KEY: Modified-site
          ( B ) LOCATION: 11
          ( D ) OTHER INFORMATION: /note= "Xaa at location 11 is
                cyclohexalanine"

( i x ) FEATURE:
          ( A ) NAME/KEY: Modified-site
          ( B ) LOCATION: 13
          ( D ) OTHER INFORMATION: /note= "Xaa at location 13 is D-Cys
                and is sulfide bonded to D-Cys at location 6"

( i x ) FEATURE:
          ( A ) NAME/KEY: Modified-site
          ( B ) LOCATION: 24
          ( D ) OTHER INFORMATION: /note= "Xaa at location 24 is
                cyclohexylalanine"

( i x ) FEATURE:
          ( A ) NAME/KEY: Modified-site
          ( B ) LOCATION: 25
          ( D ) OTHER INFORMATION: /note= "Xaa at location 25 is
                glutamic acid in the D-configuration"

( x i ) SEQUENCE DESCRIPTION: SEQ ID NO:12:

Xaa Pro Arg Pro Gly Xaa Gly Arg Gly Asp Xaa Pro Xaa Gly Asp Tyr
1               5                       10                      15

Glu Pro Ile Pro Glu Glu Ala Xaa Xaa
            20              25

( 2 ) INFORMATION FOR SEQ ID NO:13:

( i ) SEQUENCE CHARACTERISTICS:
          ( A ) LENGTH: 25 amino acids
          ( B ) TYPE: amino acid
          ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /note= "Xaa at location 1 is
                  phenylalanine in the D-configuration"

( i x ) FEATURE:
          ( A ) NAME/KEY: Modified-site
          ( B ) LOCATION: 6
          ( D ) OTHER INFORMATION: /note= "Xaa at location 6 is
                  cysteine in the D-configuration"

( i x ) FEATURE:
          ( A ) NAME/KEY: Modified-site
          ( B ) LOCATION: 11
          ( D ) OTHER INFORMATION: /note= "Xaa at location 11 is
                  norleucine"

( i x ) FEATURE:
          ( A ) NAME/KEY: Modified-site
          ( B ) LOCATION: 13
          ( D ) OTHER INFORMATION: /note= "Xaa at location 13 is
                  penicillamine in the D-configuration"

( i x ) FEATURE:
          ( A ) NAME/KEY: Modified-site
          ( B ) LOCATION: 24
          ( D ) OTHER INFORMATION: /note= "Xaa at location 24 is
                  cyclohexylalanine"

( i x ) FEATURE:
          ( A ) NAME/KEY: Modified-site
          ( B ) LOCATION: 25
          ( D ) OTHER INFORMATION: /note= "Xaa at location 25 is
                  glutamic acid in the D-configuration"

( x i ) SEQUENCE DESCRIPTION: SEQ ID NO:13:

Xaa Pro Arg Pro Gly Xaa Gly Arg Gly Asp Xaa Pro Xaa Gly Asp Tyr
1               5                       10                      15

Glu Pro Ile Pro Glu Glu Ala Xaa Xaa
            20              25

( 2 ) INFORMATION FOR SEQ ID NO:14:

( i ) SEQUENCE CHARACTERISTICS:
          ( A ) LENGTH: 25 amino acids
          ( B ) TYPE: amino acid
          ( D ) TOPOLOGY: linear ( i i ) MOLECULE TYPE: peptide ( i x ) FEATURE:
          ( A ) NAME/KEY: Modified-site
          ( B ) LOCATION: 1
          ( D ) OTHER INFORMATION: /note= "Xaa at location 1 is
                  phenylalanine in the D-configuration"

( i x ) FEATURE:

(A) NAME/KEY: Modified-site
(B) LOCATION: 6
(D) OTHER INFORMATION: /note= "Xaa at location 6 is
cysteine in the D-configuration"

(ix) FEATURE:
(A) NAME/KEY: Modified-site
(B) LOCATION: 8
(D) OTHER INFORMATION: /note= "Xaa at location 8 is
methylarginine"

(ix) FEATURE:
(A) NAME/KEY: Modified-site
(B) LOCATION: 11
(D) OTHER INFORMATION: /note= "Xaa at location 11 is
norleucine"

(ix) FEATURE:
(A) NAME/KEY: Modified-site
(B) LOCATION: 13
(D) OTHER INFORMATION: /note= "Xaa at location 13 is
penicillamine in the D-configuration"

(ix) FEATURE:
(A) NAME/KEY: Modified-site
(B) LOCATION: 24
(D) OTHER INFORMATION: /note= "Xaa at location 24 is
cyclohexylalanine"

(ix) FEATURE:
(A) NAME/KEY: Modified-site
(B) LOCATION: 25
(D) OTHER INFORMATION: /note= "Xaa at location 25 is
glutamic acid in the D-configuration"

(xi) SEQUENCE DESCRIPTION: SEQ ID NO:14:

```
Xaa Pro Arg Pro Gly Xaa Gly Xaa Gly Asp Xaa Pro Xaa Gly Asp Tyr
1               5                   10                  15
Glu Pro Ile Pro Glu Glu Ala Xaa Xaa
            20              25
```

(2) INFORMATION FOR SEQ ID NO:15:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration"

(ix) FEATURE:
(A) NAME/KEY: Modified-site
(B) LOCATION: 6
(D) OTHER INFORMATION: /note= "Xaa at location 6 is D-Cys
and is sulfide bonded to D-Cys at location 13"

(ix) FEATURE:
(A) NAME/KEY: Modified-site
(B) LOCATION: 7
(D) OTHER INFORMATION: /note= "Xaa at location 7 is
tyrosine in the D-configuration"

(ix) FEATURE:
(A) NAME/KEY: Modified-site
(B) LOCATION: 11
(D) OTHER INFORMATION: /note= "Xaa at location 11 is
norleucine"

(ix) FEATURE:
(A) NAME/KEY: Modified-site
(B) LOCATION: 13

(D) OTHER INFORMATION: /note= "Xaa at location 13 is D-Cys and is sulfide bonded to D-Cys at location 6"

(ix) FEATURE:
(A) NAME/KEY: Modified-site
(B) LOCATION: 24
(D) OTHER INFORMATION: /note= "Xaa at location 24 is cyclohexylalanine"

(ix) FEATURE:
(A) NAME/KEY: Modified-site
(B) LOCATION: 25
(D) OTHER INFORMATION: /note= "Xaa at location 25 is glutamic acid in the D-configuration"

(xi) SEQUENCE DESCRIPTION: SEQ ID NO:15:

```
Xaa Pro Arg Pro Gly Xaa Xaa Arg Gly Asp Xaa Pro Xaa Gly Asp Tyr
 1               5                  10                  15

Glu Pro Ile Pro Glu Glu Ala Xaa Xaa
            20                  25
```

(2) INFORMATION FOR SEQ ID NO:16:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is phenylalanine in the D-configuration"

(ix) FEATURE:
(A) NAME/KEY: Modified-site
(B) LOCATION: 6
(D) OTHER INFORMATION: /note= "Xaa at location 6 is D-Cys and is sulfide bonded to D-Cys at location 13"

(ix) FEATURE:
(A) NAME/KEY: Modified-site
(B) LOCATION: 7
(D) OTHER INFORMATION: /note= "Xaa at location 7 is valine in the D- configuration"

(ix) FEATURE:
(A) NAME/KEY: Modified-site
(B) LOCATION: 11
(D) OTHER INFORMATION: /note= "Xaa at location 11 is norleucine"

(ix) FEATURE:
(A) NAME/KEY: Modified-site
(B) LOCATION: 13
(D) OTHER INFORMATION: /note= "Xaa at location 13 is D-Cys and is sulfide bonded to D-Cys at location 6"

(ix) FEATURE:
(A) NAME/KEY: Modified-site
(B) LOCATION: 24
(D) OTHER INFORMATION: /note= "Xaa at location 24 is cyclohexylalanine"

(ix) FEATURE:
(A) NAME/KEY: Modified-site
(B) LOCATION: 25
(D) OTHER INFORMATION: /note= "Xaa at location 25 is glutamic acid in the D-configuration"

(xi) SEQUENCE DESCRIPTION: SEQ ID NO:16:

```
Xaa Pro Arg Pro Gly Xaa Xaa Arg Gly Asp Xaa Pro Xaa Gly Asp Tyr
 1               5                  10                  15
```

```
        Glu  Pro  Ile  Pro  Glu  Glu  Ala  Xaa  Xaa
                       20                       25
```

( 2 ) INFORMATION FOR SEQ ID NO:17:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa at location 1 is
            phenylalanine in the d-configuration"

( i x ) FEATURE:
        ( A ) NAME/KEY: Modified-site
        ( B ) LOCATION: 6
        ( D ) OTHER INFORMATION: /note= "Xaa at location 6 is D-Cys
            and is sulfide bonded to D-Cys at location 12"

( i x ) FEATURE:
        ( A ) NAME/KEY: Modified-site
        ( B ) LOCATION: 10
        ( D ) OTHER INFORMATION: /note= "Xaa at location 10 is
            norleucine"

( i x ) FEATURE:
        ( A ) NAME/KEY: Modified-site
        ( B ) LOCATION: 12
        ( D ) OTHER INFORMATION: /note= "Xaa at location 12 is D-Cys
            and is sulfide bonded to D-Cys at location 6"

( i x ) FEATURE:
        ( A ) NAME/KEY: Modified-site
        ( B ) LOCATION: 23
        ( D ) OTHER INFORMATION: /note= "Xaa at location 23 is
            cyclohexylalanine"

( i x ) FEATURE:
        ( A ) NAME/KEY: Modified-site
        ( B ) LOCATION: 24
        ( D ) OTHER INFORMATION: /note= "Xaa at location 24 is
            glutamic acid in the D-configuration"

( x i ) SEQUENCE DESCRIPTION: SEQ ID NO:17:

```
Xaa  Pro  Arg  Pro  Gly  Xaa  Arg  Gly  Asp  Xaa  Pro  Xaa  Gly  Asp  Tyr  Glu
 1                   5                        10                         15

Pro  Ile  Pro  Glu  Glu  Ala  Xaa  Xaa
                20
```

( 2 ) INFORMATION FOR SEQ ID NO:18:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa at location 1 is
            phenylalanine in the D-configuration"

( i x ) FEATURE:
        ( A ) NAME/KEY: Modified-site
        ( B ) LOCATION: 6
        ( D ) OTHER INFORMATION: /note= "Xaa at location 6 is D-Cys
            sulfide bonded to D-Cys at location 13"

( i x ) FEATURE:

(A) NAME/KEY: Modified-site
(B) LOCATION: 7
(D) OTHER INFORMATION: /note= "Xaa at location 7 is
threonine in the D-configuration"

(ix) FEATURE:
(A) NAME/KEY: Modified-site
(B) LOCATION: 11
(D) OTHER INFORMATION: /note= "Xaa at location 11 is
norleucine"

(ix) FEATURE:
(A) NAME/KEY: Modified-site
(B) LOCATION: 13
(D) OTHER INFORMATION: /note= "Xaa at location 13 is D-Cys
sulfide bonded to D-Cys at location 6"

(ix) FEATURE:
(A) NAME/KEY: Modified-site
(B) LOCATION: 24
(D) OTHER INFORMATION: /note= "Xaa at location 24 is
cyclohexylalanine"

(ix) FEATURE:
(A) NAME/KEY: Modified-site
(B) LOCATION: 25
(D) OTHER INFORMATION: /note= "Xaa at location 25 is
glutamic acid in the D-configuration"

(xi) SEQUENCE DESCRIPTION: SEQ ID NO:18:

Xaa Pro Arg Pro Gly Xaa Xaa Arg Gly Asp Xaa Pro Xaa Gly Asp Tyr
1               5                   10                  15

Glu Pro Ile Pro Glu Glu Ala Xaa Xaa
            20              25

(2) INFORMATION FOR SEQ ID NO:19:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylalanine in the D-configuration"

(ix) FEATURE:
(A) NAME/KEY: Modified-site
(B) LOCATION: 6
(D) OTHER INFORMATION: /note= "Xaa at location 6 is D-Cys
sulfide bonded to D-Cys at location 13"

(ix) FEATURE:
(A) NAME/KEY: Modified-site
(B) LOCATION: 7
(D) OTHER INFORMATION: /note= "Xaa at location 7 is
proline in the D-configuration"

(ix) FEATURE:
(A) NAME/KEY: Modified-site
(B) LOCATION: 11
(D) OTHER INFORMATION: /note= "Xaa at location 11 is
norleucine"

(ix) FEATURE:
(A) NAME/KEY: Modified-site
(B) LOCATION: 13
(D) OTHER INFORMATION: /note= "Xaa at location 13 is D-Cys
sulfide bonded to D-Cys at location 6"

(ix) FEATURE:
(A) NAME/KEY: Modified-site
(B) LOCATION: 24

(D) OTHER INFORMATION: /note= "Xaa at location 24 is
cyclohexylalanine"

(ix) FEATURE:
(A) NAME/KEY: Modified-site
(B) LOCATION: 25
(D) OTHER INFORMATION: /note= "Xaa at location 25 is
glutamic acid in the D-configuration"

(xi) SEQUENCE DESCRIPTION: SEQ ID NO:19:

Xaa Pro Arg Pro Gly Xaa Xaa Arg Gly Asp Xaa Pro Xaa Gly Asp Tyr
1               5                   10                  15

Glu Pro Ile Pro Glu Glu Ala Xaa Xaa
            20              25

(2) INFORMATION FOR SEQ ID NO:20:

(i) SEQUENCE CHARACTERISTICS:
(A) LENGTH: 25 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note= "Xaa at location 1 is
phenylglycine in the D-configuration"

(ix) FEATURE:
(A) NAME/KEY: Modified-site
(B) LOCATION: 6
(D) OTHER INFORMATION: /note= "Xaa at location 6 is D-Cys
sulfide bonded to D-Cys at location 13"

(ix) FEATURE:
(A) NAME/KEY: Modified-site
(B) LOCATION: 11
(D) OTHER INFORMATION: /note= "Xaa at location 11 is
norleucine"

(ix) FEATURE:
(A) NAME/KEY: Modified-site
(B) LOCATION: 13
(D) OTHER INFORMATION: /note= "Xaa at location 13 is D-Cys
sulfide bonded to D-Cys at location 6"

(ix) FEATURE:
(A) NAME/KEY: Modified-site
(B) LOCATION: 24
(D) OTHER INFORMATION: /note= "Xaa at location 24 is
cyclohexylalanine"

(ix) FEATURE:
(A) NAME/KEY: Modified-site
(B) LOCATION: 25
(D) OTHER INFORMATION: /note= "Xaa at location 25 is
glutamic acid in the D-configuration"

(xi) SEQUENCE DESCRIPTION: SEQ ID NO:20:

Xaa Pro Arg Pro Gly Xaa Gly Arg Gly Asp Xaa Pro Xaa Gly Asp Tyr
1               5                   10                  15

Glu Pro Ile Pro Glu Glu Ala Xaa Xaa
            20              25

(2) INFORMATION FOR SEQ ID NO:21:

(i) SEQUENCE CHARACTERISTICS:
(A) LENGTH: 25 amino acids
(B) TYPE: amino acid
(D) TOPOLOGY: linear (ii) MOLECULE TYPE: peptide ( i x ) FEATURE:
    ( A ) NAME/KEY: Modified-site
    ( B ) LOCATION: 1
    ( D ) OTHER INFORMATION: /note= "Xaa at location 1 is
        1,2,3,4- tetrahydroisquinoline-3-carboxylic acid in
        the D- configuration"

( i x ) FEATURE:
    ( A ) NAME/KEY: Modified-site
    ( B ) LOCATION: 6
    ( D ) OTHER INFORMATION: /note= "Xaa at location 6 is D-Cys
        sulfide bonded to D-Cys at location 13"

( i x ) FEATURE:
    ( A ) NAME/KEY: Modified-site
    ( B ) LOCATION: 11
    ( D ) OTHER INFORMATION: /note= "Xaa at location 11 is
        noreleucine"

( i x ) FEATURE:
    ( A ) NAME/KEY: Modified-site
    ( B ) LOCATION: 13
    ( D ) OTHER INFORMATION: /note= "Xaa at location 13 is D-Cys
        sulfide bonded to D-Cys at location 6"

( i x ) FEATURE:
    ( A ) NAME/KEY: Modified-site
    ( B ) LOCATION: 24
    ( D ) OTHER INFORMATION: /note= "Xaa at location 24 is
        cyclohexylalanine"

( i x ) FEATURE:
    ( A ) NAME/KEY: Modified-site
    ( B ) LOCATION: 25
    ( D ) OTHER INFORMATION: /note= "Xaa at location 25 is
        glutamic acid in the D-configuration"

( x i ) SEQUENCE DESCRIPTION: SEQ ID NO:21:

```
Xaa Pro Arg Pro Gly Xaa Gly Arg Gly Asp Xaa Pro Xaa Gly Asp Tyr
1               5                   10                  15

Glu Pro Ile Pro Glu Glu Ala Xaa Xaa
            20              25
```

( 2 ) INFORMATION FOR SEQ ID NO:22:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa at location 1 is
            N- methylphenylalanine in the D-configuration"

( i x ) FEATURE:
        ( A ) NAME/KEY: Modified-site
        ( B ) LOCATION: 6
        ( D ) OTHER INFORMATION: /note= "Xaa at location 6 is D-Cys
            sulfide bonded to D-Cys at location 13"

( i x ) FEATURE:
        ( A ) NAME/KEY: Modified-site
        ( B ) LOCATION: 11
        ( D ) OTHER INFORMATION: /note= "Xaa at location 11 is
            norleucine"

( i x ) FEATURE:
        ( A ) NAME/KEY: Modified-site
        ( B ) LOCATION: 13
        ( D ) OTHER INFORMATION: /note= "Xaa at location 13 is D-Cys
            sulfide bonded to D-Cys at location 6"

(ix) FEATURE:
    (A) NAME/KEY: Modified-site
    (B) LOCATION: 24
    (D) OTHER INFORMATION: /note= "Xaa at location 24 is cyclohexylalanine"

(ix) FEATURE:
    (A) NAME/KEY: Modified-site
    (B) LOCATION: 25
    (D) OTHER INFORMATION: /note= "Xaa at location 25 is glutamic acid in the D-configuration"

(xi) SEQUENCE DESCRIPTION: SEQ ID NO:22:

```
Xaa Pro Arg Pro Gly Xaa Gly Arg Gly Asp Xaa Pro Xaa Gly Asp Tyr
 1               5                   10                  15
Glu Pro Ile Pro Glu Glu Ala Xaa Xaa
            20              25
```